United States Patent [19]
Chung et al.

[11] Patent Number: 5,679,636
[45] Date of Patent: Oct. 21, 1997

[54] BONE AND PROSTATE-DERIVED PROTEIN FACTORS AFFECTING PROSTATE CANCER GROWTH, DIFFERENTIATION, AND METASTASIS

[75] Inventors: Leland W. K. Chung, Houston; James C. Chan, Sugarland; Christopher J. Logothetis, Houston, all of Tex.

[73] Assignee: Board of Regents, The University of Texas, Austin, Tex.

[21] Appl. No.: 341,297

[22] Filed: Nov. 15, 1994

Related U.S. Application Data

[63] Continuation of Ser. No. 859,228, Mar. 30, 1992, abandoned.

[51] Int. Cl.$^6$ .................. A61K 38/18; C07K 14/475; A23J 1/00
[52] U.S. Cl. .................. 514/2; 530/399; 530/350; 530/412; 530/413
[58] Field of Search .................. 514/2; 530/350, 530/399, 412, 413

[56] References Cited

PUBLICATIONS

M. Chackal–Roy and B.R. Zetter, *Faseb Journal*, 4(7):A1989, 1990, Abstract No. 1723.

M. Chackal–Roy et al., "Stimulation of Human Prostatic Carcinoma Cell Growth by Factors Present in Human Bone Marrow," *The American Society for Clinical Investigation, Inc.*, 84:43–50, 1989.

Leland W.K. Chung, "Fibroblasts Are Critical Determinants in Prostatic Cancer Growth and Dissemination," *Cancer and Metastasis Reviews*, 10:263–274, 1991.

Leland, W.K. Chung et al., "Reciprocal Mesenchymal–Epithelial Interaction Affecting Prostate Tumor Growth an Hormonal Responsiveness," *Cancer Surveys*, 11:91–121, 1991.

Martin Gleave et al., "Acceleration of Human Prostate Cancer Growth in Vivo by Factors Produced by Prostate and Bone Fibroblasts," *Cancer Research*, 51:3753–3761, 1991.
Martin Gleave et al., *Journal of Urology*, 145(4 Suppl.), 213A, 1991, Abstract No. 1.

M.E. Gleave et al., "Prostate and Bone Fibroblasts Induce Human Prostate Cancer Growth in Vivo: Implications for Bidirectional Tumor–Stromal Cell Interaction in Prostate Carcinoma Growth and Metastasis," *Journal of Urology*, 147:1151–1159, 1992.

Martin E. Gleave et al., "Serum Prostate Specific Antigen Levels in Mice Bearing Human Prostate LNCaP Tumors Are Determined by Tumor Volume and Endocrine and Growth Factors," *Cancer Research*, 52:1598–1605, 1992.

Zetter, Bruce R. et al., "Selective Stimulation of Prostatic Carcinoma Cell Proliferation by Transferrin," *Proceedings of the National Academy of Science*, 89:6197–6201, 1992.

Dialog Search Report, 1992.

*Primary Examiner*—Robert A. Wax
*Assistant Examiner*—Karen Cochran Carlson
*Attorney, Agent, or Firm*—Arnold, White & Durkee

[57] ABSTRACT

The role of tumor cell-host stromal interaction and stromal-specific growth factors in prostate cancer growth, progression and metastasis to the axial skeleton were investigated. Following co-inoculation of athymic mice with human prostate cancer cells (LNCaP) and various nontumorigenic fibroblasts, human prostate-like tumor formation was consistently induced by human bone (MS) fibroblasts (62%), embryonic rat urogenital sinus mesenchymal (rUGM) cells (31%) and Noble rat prostatic fibroblasts (17%), but not by NIH-3T3, normal rat kidney (NRK), or human lung CCD16 fibroblasts. Carcinomas formed preferentially in male hosts, demonstrating in vivo androgen sensitivity. A novel in vivo method in which a slowly adsorbed matrix (Gelfoam) was employed to deliver concentrated prostate and bone fibroblast-derived conditioned media was also found to induce LNCaP tumor formation in vivo. Such in vivo growth-promoting effects correlated with in vitro tests employing a soft agar colony-forming assay using rat prostate epithelial (NbE-1) cells as targets. A substantially purified human growth factor preparation is shown to contain distinct polypeptides with apparent $M_r$s on SDS/PAGE of 227, 223, 218, 157, 90, 80, 48, and 20 kD, and to be distinct from bFGF. The human growth factor polypeptide of 157 kD was identified, in human bone marrow aspirates, by immunoblotting with the mAb MS 329.

1 Claim, 11 Drawing Sheets

FIG. 7A
| GELFOAM® TREATMENT | TUMOR FORMATION ($2 \times 10^6$ LNCaP) |
| --- | --- |
| COLLAGEN IV ALONE | 0/6 (0%) |
| COLLAGEN IV + ECGF | 0/6 (0%) |
| COLLAGEN IV + bFGF | 3/5 (60%) |
| COLLAGEN IV + rUGM CM | 5/10 (50%) |
| COLLAGEN IV + MS CM | 3/8 (38%) |
FIG. 7B
FIG. 7C
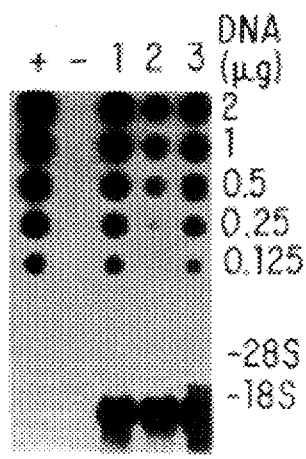
FIG. 7D

BONE AND PROSTATE-DERIVED PROTEIN FACTORS AFFECTING PROSTATE CANCER GROWTH, DIFFERENTIATION, AND METASTASIS

This is a continuation of application Ser. No. 07/859,228, filed Mar. 30, 1992, now abandoned.

The government may own rights in the present invention pursuant to grant number IR01-CA-56307-01 from the National Cancer Institute.

BACKGROUND OF THE INVENTION

1. Field of the Invention

The present invention relates generally to the field of cancer and also to polypeptides with growth-promoting activities. The invention is particularly directed to the identification of growth factors, primarily from bone and prostate tissues, that have the capability to stimulate the growth of prostate cells and which promote the metastasis of prostate cancer to bone tissues. The invention is further directed to novel in vivo and in vitro assay methods, both to detect and quantitate such growth factor activity, and to screen for potential anti-cancer therapeutic substances. The preparation and use of monoclonal antibodies against such growth factor polypeptides is also disclosed.

2. Description of the Related Art

The increased incidence of prostate cancer during the last decade has established prostate cancer as both the most prevalent cancer, and the second leading cause of cancer deaths, in men (Carter & Coffey, 1990). Most patients dying of prostate cancer experience painful and sometimes crippling osseous metastases with up to 84% having bony metastases at autopsy (Franks, 1956). Prostate cancer is known to selectively spread to the cancellous bones of the axial skeleton, where it is the only malignancy to consistently produce osteoblastic lesions (Cook & Watson, 1968). Frequently, these bony metastatic lesions grow at a more rapid rate than that of primary or other metastatic lesions (Jacobs, 1983).

The treatment strategies available for patients with metastatic prostate cancer have, in the past, focused primarily on androgen deprivation and/or radiation therapy. Such therapeutic modalities have palliative value, but have not resulted in cure or significant increases in patient survival rate. Recently, suramin, a drug known to disrupt the interaction of growth factors and their receptors, was shown to inhibit prostate tumor cell growth both in vitro and in vivo (LaRocca et al., 1990). However, the extreme toxicity of suramin in vivo prevents its clinical use in human treatment.

The "seed and soil" hypothesis initially described in 1989 (Paget, 1989), proposes that tumor cells may selectively grow in certain organs due to their particular properties. More recently, some such properties have been proposed to be relevant to prostate cancer development, including, enhanced adhesion (Nicolson & Winkelhake, 1975; Sherman et al., 1980), chemotaxis (Varani, 1982; Hujanen & Terranova, 1985), or preferential growth at certain sites (Manishen et al., 1985; Hart, 1985).

Several factors have been hypothesized to be responsible for the metastasis of prostate cancer to bone tissues. For example, it has been proposed that prostate cancer cells selectively seed the lumbar spine and pelvis via a paravertebral venous plexus through which retrograde flow from the prostate to the spine may occur at times of increased intraabdominal pressure (Batson, 1940; Shevrin et al., 1988). However, this theory falls short as most tumor cells in the venous circulation also pass through the lungs (Nicolson, 1979) and yet the incidence of clinically apparent lung metastases in patients dying of prostate cancer is low (Elkin & Mueller, 1979; Johnson, 1982). Furthermore, kinetic distribution studies using radiolabelled tumor cells have not shown a correlation between organ seeding and subsequent metastatic formation (Fidler & Nicolson, 1976; Potter et al., 1983), suggesting that factors other than the simple mechanical arrest of tumor cells are responsible for the development of prostate cancer bony metastasis.

Recent work has provided some evidence that prostate cancer cell growth may be under autocrine influences involving androgen-mediated regulation of TGFα, EGF receptor, or bFGF (Wilding et al., 1989; Nonomura et al., 1988; Lu et al., 1989). It has also been suggested that paracrine-mediated pathways involving the stromal compartment play a role in prostate cancer progression (Camps et al., 1990; Chung et al., 1989; Chackel-Roy et al., 1989; Kabalin et al., 1989). Clinically, the interaction between prostate cancer cells and osteoblasts is apparent from the enhanced growth rate of bony metastatic lesions and accompanying osteoblastic reaction. Primary benign and malignant prostatic neoplasms have been shown to express bFGF (Mydlo et al., 1988; Story et al., 1987). Prostatic osteoblastic factor, a soluble substance found in benign hyperplastic and malignant prostatic tissue that stimulates osteoblasts, may well be a FGF-like substance (Jacobs et al., 1979; Nishi et al., 1988), although it may be a distinct and as yet undefined growth factor (Perkel et al., 1990).

Despite many studies, including those described above, it is evident that the factors involved in prostatic carcinogenesis, progression and nonrandom metastasis remain poorly defined. Moreover, the actions of those few growth factors which have been shown to stimulate prostate cell growth in vitro have not been examined in vivo. The identification of growth factor(s) which exhibit prostate cell growth promoting activity in vivo would be an important development, creating new avenues of clinical investigation and treatment.

The current lack of information concerning the in vivo action of such growth factors highlights another drawback which currently exists in the art, that is the lack of an appropriate animal model with which to investigate the many inter-relating factors which may contribute to the progression and metastasis of prostate cancer. This is particularly important as only an in vivo human prostate cancer model is appropriate to asses the complicated mechanisms underlying the metastatic process, which naturally, cannot be assessed solely in vitro.

SUMMARY OF THE INVENTION

Accordingly, the present invention is directed to the identification and purification of novel growth factors, primarily present in bone tissues, but also present in prostate tissues, that have the capability to promote normal prostate cell growth and prostate cancer cell growth and metastases. The invention is further directed to novel in vivo assay methods, both for the identification of factors which promote prostate cancer cell growth, and to the identification of potential therapeutic compounds for use in treatment strategies. The present invention further encompasses the generation of monoclonal antibodies directed against these growth factor polypeptides and their use in cancer diagnosis and treatment.

The growth-promoting factor(s) of the present invention are defined as containing proteins or polypeptides, including extracellular matrix protein(s) and polypeptide(s), that have the capability to stimulate prostate cell growth. As used herein, the term "stimulate prostate cell growth" is intended to refer to the capacity of a given composition to promote the growth or proliferation of normal, or cancerous, prostate cells to any detectable degree. Accordingly, the growth factor of the present invention is functionally characterized as having the ability to stimulate the growth of prostate cells, as exemplified by an ability to stimulate the growth of normal prostate cells in culture; or the ability to stimulate the growth of prostate cancer cells such as LNCaP cells.

Further to the functional characterization described above, the growth factor of the present invention is particularly characterized as comprising one, or a combination of, polypeptides being selected from the group consisting of polypeptides characterized as exhibiting an apparent molecular weight on SDS/PAGE, when conducted as described hereinbelow, of approximately: 227, 223, 218, 157, 90, 80, 48, and 20 kD. However, it is, of course, generally understood by those of skill in the art that the migration of a polypeptide can vary with different conditions of SDS/PAGE (Capaldi et al., 1977). It will therefore be appreciated that under differing electrophoretic conditions, the molecular weight assignments quoted above may vary.

It will be further understood that certain of the polypeptides may be present in quantities below the detection limits of the Coomassie brilliant blue staining procedure usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of each of the polypeptides present within the growth factor. Immunologically-based techniques such as Western blotting using enzymatically-, radiolabel-, or fluorescently-tagged secondary antibodies are considered to be of particular use in this regard.

In important embodiments, the present invention concerns the substantial purification of such prostate cell growth-promoting factor(s) from human bone tissues. The term "substantially purified human growth factor", as used herein, refers to a growth factor composition, isolatable from human bone fibroblasts, from which has been removed various non-growth-promoting components, and which composition substantially retains its prostate cell growth promoting activity.

Further embodiments of the present invention relate to methods of purifying one or more of the foregoing growth factors. A particularly preferred source for isolating such growth factors is the cell-conditioned media obtained from human bone or prostate fibroblasts. Such conditioned media were chosen by the inventors as a potential sources of prostate cell growth factors because of the frequent metastasis of prostate cancer to the axial skeleton. In that the human bone fibroblast conditioned media was found to be a particularly rich source of growth factors, it is contemplated to be the preferred starting material for the purification of such growth factors. However, other starting materials may also be employed such as, for example, human prostate cancers, human osteogenic sarcomas, or bone marrow aspirates, preferably obtained from prostate cancer patients.

The preferred approach used to isolate such growth factors involves first culturing human bone fibroblasts to produce the human growth factor polypeptides. After obtaining the growth factor polypeptides, for example, by removing conditioned media from the cells, the resultant cell-free polypeptides can then be assayed, characterized and used as a starting material for further purification of the growth factors. During the purification process, it is contemplated that assays will be conducted at various intervals using any one of, or a combination of, the assays methods disclosed herein.

The method preferred by the present inventors to obtain a substantially purified human growth factor in accordance herewith is affinity chromatography, and in particular, affinity chromatography employing a heparin sepharose column. To perform heparin sepharose chromatography in this manner one would first pass a sample of the cell-free growth factor polypeptides, for example, as contained within conditioned media, over the column in a low salt containing buffer, such as 10 mM Tris/HCl, 1 mM PMSF, pH 7.4, to allow binding to the column, and then wash the column with the same buffer to remove any non-binding species. The components that bind to the column can be eluted using the above buffer with an increased salt concentration, such as 1 M or 2 M NaCl, or by employing a buffered salt gradient, for example, of 0–3 M NaCl. Following assays of the eluted material the active fractions can be identified, and such fractions selected and pooled.

The growth factors of the present invention are proposed to have utility in a variety of embodiments. Importantly, they are contemplated to be of use in vivo in stimulating the growth of prostate grafts. Also, in that the tumor formed under the stimulation of these growth factors was found to be extremely angiogenic, the growth factors of the present invention are also reasoned to be powerful angiogens, and as such are contemplated to have utility in further clinical embodiments. These include, for example, the promotion of wound healing, organ growth and/or regeneration, and the promotion of epithelial sprouting.

Furthermore, the growth factors can be used either alone, or in conjunction with other components, in novel tissue culture media. Although preferred, there is no general requirement that the growth factors be provided in their most purified state for use in such embodiments, indeed, it is contemplated that conditioned media containing the growth factors could be suitably directly employed in tissue culture protocols.

Various methods are contemplated to be of use in determining prostate cell growth, i.e., for use in assaying the activity of prostate growth-promoting factors. In preferred embodiments, it is contemplated that such assays may be directed to analyzing the growth of prostate cancer cells, rather than normal prostate cells, simply as a matter of convenience. Such assays include, but are not limited to, in vitro assays such as the uptake and elution of crystal violet dye; the MTT assay for staining and quantitation of live cells in a culture dish; or the incorporation of radioactive, or non-radioactive labels, such as $^3$H-thymidine, or bromodeoxy uridine, respectively, into TCA-precipitable cellular DNA.

A preferred in vitro assay for use in accordance with the present invention is contemplated to be the soft agar colony-forming assay. The soft agar colony-forming assay is an indication of transformation, as only transformed cell types can grow in soft agar. Methods of conducting an assay of this kind will be known to those of skill in the art in light of the present disclosure. For example, one could first place placing agar, such as 0.6% (w/v) agar, into the bottom of each well on a plate, and seed the wells with an appropriate number of NbE-1 cells, such as 2,000 cells. A feeder layer of less concentrated agar, such as 0.3 to 0.4% (w/v) agar, containing the potential growth factor substances to be analyzed, would then be placed on top of the cells, from which the candidate substances can diffuse and come into contact with the cells. The number of soft agar colonies subsequently formed would be recorded after an appropriate time interval, for example, on the order of 3 to 4 weeks after seeding. Both the cells and the agar could then be prepared and resuspended in media such as T-medium containing approximately between 5 and 10% foetal calf serum if desired.

A particularly important aspect of the present invention is the development of a novel in vivo assay for prostate cancer growth promoting activity. The development of such an assay is based on the inventors' observations that although LNCaP human prostate cancer cells are nontumorigenic when administered at a dose of $<5 \times 10^6$ cells/site, to athymic mice, cancer formation can be induced following co-administration of the non-tumorigenic prostate cells with other cells or compositions. This method therefore allows the inductive capabilities of any cell type, conditioned media, growth factor, hormone, carcinogen, or indeed, any substance one desires, to be examined following the co-administration of the substance and LNCaP cells, or other nontumorigenic human cells, to mice.

The choice of LNCaP cells for use in such an assay is particularly preferred as such cells have certain advantageous features. For example, LNCaP cells produce prostate specific antigen (PSA), a human tissue-specific tumor marker, which can be as one method to monitor in vivo prostate cancer cell growth. Moreover, LNCaP cells are the only androgen-responsive human prostate cancer cells that can be consistently grown in vitro. This is an important aspect of the invention that allows one to conduct parallel in vitro and in vivo assays of various compounds using the same prostate cancer cell types.

To conduct such an assay to investigate the capability of a given cell type to elicit LNCaP growth in vivo, one would preferably co-inoculate suitable athymic mice, such as 6-8 week old BALB/c mice, with a number of LNCaP cells and an approximately equivalent number of cells of the cell type to be investigated (herein referred to as the "subject cell type"). Virtually any mode of co-inoculation is considered to be appropriate such as subcutaneous, intravenous, or intraperitoneal injection. The administration of $1 \times 10^5$ to $5 \times 10^6$ cells per inoculant of each cell type is preferred, with the administration of $1 \times 10^6$ LNCaP cells and $1 \times 10^6$ of the subject cells being particularly preferred. One would suspended the cells in an appropriate medium, such as RPMI 1640 with 10% foetal bovine serum (FBS), prior to injection.

It is contemplated that one would also generally wish to perform parallel control experiments to confirm the nontumorigenic nature of the LNCaP and subject cells when administered independently. In such control studies one would administer the same number, or slightly more cells, such as in the order of $2 \times 10^6$ to $5 \times 10^6$ of each cell type.

Various methods are contemplated to be of use in assessing tumor development. The tumors can be measured at regular intervals and their volumes calculated according to the formula L×W×H×0.5236 (Janek et al., 1975). After sacrifice, the tumors may be excised, weighed, and subjected to various morphological and biochemical analyses as desired. Furthermore, the choice of LNCaP cells by the inventors also allows the serum levels PSA to be used as an indication of tumor progression.

In further important embodiments, the present invention provides modifications of this in vivo assay model which have been developed to allow the investigation of the effects of substances other than intact cells on prostate cancer growth. This modified method is based upon the adsorption of a concentrated substance onto a solid matrix and the co-administration of the matrix and LNCaP cells to the experimental animal. The adsorbed matrix serves as a reservoir for delivery of the particular substance to the live animal. It is contemplated that this method will be particularly useful for analyzing substances such as conditioned media from various cell types and the partially and fully purified growth factors.

To conduct such an assay one would modify the protocol described immediately above by substituting the co-administration of LNCaP cells with subject cells for the co-administration of LNCaP cells with the adsorbed matrix. A particularly preferred matrix for use in such embodiments is Gelfoam which is commercially available from Upjohn (Kalamazoo, Mich.), although it is believed that any sponge-like matrix, such as, for example, Matrigel, or even agar or agrose, may be employed. One would prepare the matrix under sterile conditions by firstly pre-soaking it with collagen IV, for example by exposure to 100 µg/ml collagen IV for 12 hours at 4° C., and then exposing it to the test compound(s). The adsorbed matrix would then be minced to allow subcutaneous inoculation, for example using a polytron. A suitable control for an assay such as this would be inoculation with Gelfoam pre-soaked with collagen IV alone.

In that either of the above methods can be utilized to generate an animal bearing a human prostate cancer, the present invention further provides an important model for use in screening for compounds with the potential to inhibit the growth of human prostate cancer. To screen for a substance having the capability to inhibit, retard, or otherwise exert a negative effect on prostate cancer cell growth, one may administer the test substance either simultaneously with, or subsequent to, the administration of the cancer promoting agents, i.e., the LNCaP cells and the previously identified stimulatory cells or substances. One would then determine the effect of the candidate inhibitory substance by measuring the degree of tumor formation or regression, or the prevention or inhibition of tumor growth, observed in the presence of the candidate inhibitory substance and comparing it to the tumor status in the absence of the potentially inhibitory substance.

In still further embodiments, the present invention concerns the generation of antibodies, and particularly, monoclonal antibodies (mAbs) against the growth factor polypeptide(s) disclosed herein. Such mAbs will have utility in a variety of applications. These include, for example, the rapid purification of the growth factors by immunoaffinity chromatography, and the clinical use of mAbs or mAb-conjugates in diagnostic, prognostic, imaging, and therapeutic strategies for the treatment of prostate cancer in man.

The in vivo human prostate cancer model disclosed herein is contemplated to be particularly useful in testing mAbs to identify those that are suitable for clinical use. For example, one may test the ability of mAbs or mAb-conjugates to inhibit prostate cancer growth or metastasis in the mouse model, prior to clinical trials in human subjects. It will be understood, however, that mAbs which are not considered to meet the criteria for clinical use may nonetheless have utility in other embodiments, such as in growth factor purification by affinity column chromatography or in Western blotting, ELISA, or other immunological screening assays.

It is proposed that such anti-growth factor mAb generation may be achieved most readily through the use of a modified immunization protocol. It is contemplated that the initial immunization of an experimental animal, such a mouse, would be performed according to the standard practice in the art. However, for the booster inoculation, the use of the following method is proposed to be advantageous in that it will allow the optimal exposure of splenocytes to the booster antigen. The immunized mice should be surgically opened to expose the spleen and a sterile solution of the growth factor antigens be injected directly into the spleen. The mouse would then be sutured and allowed to recover.

Blood samples of the immunized mice may be analyzed for the presence of circulating antibodies to the growth factors, and those mice producing reasonable titers of circulating antibodies would be sacrificed and their spleens will be removed for cell fusion. A mouse myeloma cell line proposed to be of use for hybridization is the S-azaguanine-resistant mouse murine myeloma SP2/0 non-producer cell line, which is known to be HAT sensitive. Cells may be fused according to any of the methods known in the art, such as, by using polyethylene glycol (PEG), and later screened for antibody production, for example, by employing an ELISA or immunoblot technique.

BRIEF DESCRIPTION OF THE DRAWINGS

FIGS. 7a–d. rUGM and MS conditioned media stimulate LNCaP tumor growth in vivo. Gelfoam, a solid form of slowly absorbable gelatin, was used as a reservoir for delivery of biologically active factors to determine whether LNCaP tumor growth could be induced by fibroblast conditioned media in vivo in the absence of stromal cells. Gelfoam was adsorbed with 100 μg/ml collagen IV for 12 hours followed by ECGF, bFGF, or stromal conditioned media. LNCaP cells, $2\times10^6$, were inoculated s.c. with treated Gelfoam, except at some control sites, where ECGF-treated Gelfoam was injected alone to detect angiogenesis. Angiogenesis was visible after 3 weeks when Gelfoam plus collagen IV adsorbed with ECGF was injected (b). At rUGM conditioned media-treated sites, 5 of 10 (50%) tumors formed by 10 weeks (mean tumor volume, 278 $mm^3$). With MS conditioned media-treated Gelfoam, 3 tumors formed at 8 sites (38%). bFGF was also tested because of its in vitro mitogenic activity and induced tumor formation at 3 of 5 sites (60%). All tumors were histologically carcinomas and stained intensely and uniformly for PSA (c). Southern blot analysis for Alu and corresponding Northern analysis for PSA expression are both positive (d).

DETAILED DESCRIPTION OF THE PREFERRED EMBODIMENTS

Figure 1A:
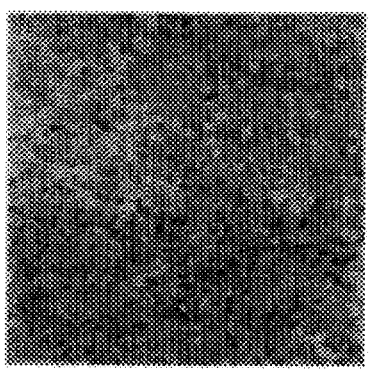
FIGS. 1a–f. Histomorphological and immunohistochemical characterization of fibroblast-induced LNCaP chimeric tumors. Hematoxylin and eosin-stained sections (a–c) reveal differences between LNCaP/rUGM tumors in male (a) and female (b) hosts, the former a carcinosarcoma, the latter a pure sarcoma with no epithelial component. LNCaP/MS tumors (c) formed only in male hosts and histologically are vascular carcinomas with a minor mesenchymal component. Immunohistochemical staining with monoclonal antibodies against PSA (d–f) demonstrates intense and generalized staining of the epithelial cells in only male LNCaP/rUGM (d) and LNCaP/MS (f) tumors but not of the sarcomatoid LNCaP/rUGM tumors (e) in female mice. LNCaP/3T3 tumors are sarcomas histologically similar to LNCaP/rUGM tumors in females and also stained negatively for PSA.

Cellular interactions between mesenchymal and epithelial cells are believed to be an integral part of embryonic development (Kratochwil, 1972) which continues through adulthood by maintaining differentiated organ growth and function (Frank et al., 1970). These interactions have also been proposed to be involved in the regulation of hormonal responsiveness (Cunha & Chung, 1981) and may play an important inductive and/or permissive role in the pathogenesis of tumor growth (Pitot et al., 1985; DeCosse et al., 1973; Hodges et al., 1977) and metastases (Chackel-Roy et al., 1989; Horak et al., 1985). The growth of a number of epithelial malignancies are influenced by their surrounding stroma, including the urinary bladder (Camps et al., 1990; Hodges et al., 1977), prostate (Camps et al., 1990; Kabalin et al., 1989), colon (Picard et al., 1986), and breast (Miller et al., 1989).

The present disclosure presents the results from studies directed to identification and characterization of growth factors which promote prostate cell growth. Also examined is the question of whether fibroblast-specificity exists in affecting the growth of human prostate cancer, and in particular, of the lymph node derived prostate cancer cell line (LNCaP).

LNCaP cells were chosen for several reasons. Firstly, LNCaP cells have previously been shown to be nontumorigenic when injected subcutaneously in athymic mice with less than $4 \times 10^6$ cells/inoculum (Horoszewicz et al., 1983). This observation was confirmed by the present inventors, and further extended by their discovery that LNCaP cells are nontumorigenic even at higher doses. Thus the inductive capabilities of specific fibroblasts can be examined following their co-administration to mice along with LNCaP. Secondly, the LNCaP cell line is the only prostate cell line that produces prostate specific antigen (PSA) (Papsidero et al., 1981), a human tissue-specific tumor marker used clinically to monitor in vivo prostate cancer cell growth (Stamey et al, 1987; Ford et al., 1985). Thirdly, LNCaP cells are androgen-responsive both in vivo (Sonnenschein et al., 1989) and in vitro (Schuurmans et al., 1989) which provides scope for the sex-dependent differences in chimeric tumor growth to be assessed.

Furthermore, and importantly, of the androgen-responsive human prostate cancer models available, including PC82, HONDA, and LNCaP cell lines, only the LNCaP can be consistently grown in vitro (Isaacs, 1987). The inventors have exploited these properties in the development of parallel in vitro and in vivo cell-cell interaction assays. This allows, for the first time, the results from dual model systems using the same cell types and factors to be assessed. Moreover, results from such co-ordinated in vitro and in vivo studies can be more confidently applied to the clinical situation.

The in vivo assay system disclosed herein is based upon the co-administration of LNCaP cells to athymic mice along with another cell type or composition. The effect of the cells or composition being analyzed can then be assessed by determining the degree of tumor growth in the co-inoculated animals and comparing it the control growth observed (if any) in animals given either LNCaP cells, or the test composition, alone.

To analyze compositions other than intact cells, the inventors have developed a modified version of the assay. This is based upon the adsorption of concentrated substance(s) onto a solid matrix and the co-administration of the matrix and LNCaP cells to an experimental animal where the adsorbed matrix acts as a reservoir for the in vivo delivery of the test substance(s). It is contemplated that this method will be particularly useful for analyzing substances such as conditioned media from various cell types and known growth factors.

The results disclosed herein demonstrate that certain fibroblasts can induce LNCaP tumor growth in vivo in a cell-type specific and androgen-dependent manner. Of the 6 fibroblast cell lines analyzed, bone fibroblasts, followed by the prostate-derived fibroblasts, were found to be the most effective in stimulating LNCaP cell growth both in vivo and in vitro. The presence of bidirectional paracrine pathways between LNCaP and fibroblast cells is illustrated in vivo by the development of sarcomas with the co-inoculation of LNCaP cells and nontumorigenic rUGM and 3T3 fibroblasts. Similar effects are also apparent in vitro as LNCaP and rUGM conditioned media produce bidirectional increases in growth in a paracrine-, but not autocrine-, mediated fashion. These observations suggest that LNCaP and fibroblast cells secrete factors that produce a more favorable microenvironment for tumorigenesis by reciprocally promoting growth, adherence or angiogenesis.

LNCaP cells participated in chimeric tumor formation preferentially in males, demonstrating initial in vivo androgen-sensitive growth. These results, along with their in vitro androgen sensitivity, further support the view that the initial growth of LNCaP cells in vivo may be androgen-responsive (Sonnenschein et al., 1989).

Using this novel method, the LNCaP androgen-refractory cell lines, $C_4$ and $C_5$ have been shown, for the first time, to be tumorigenic and to secrete high levels of PSA autonomously, i.e., in the absence of androgen. Both of these characteristics are typically found in human prostate cancer as it undergoes transformation to enter the hormonally refractory state. Furthermore, the inventors' finding that hormonally refractory prostate cancer cells secrete specific autocrine protein factor(s) that induce PSA gene expression by the prostate cells is important as, to date, there have been no reports concerning this area of investigation. The identification of factor(s) produced by such refractory cells may impact on the development of new therapeutic approaches to address the problem of hormonally refractory prostate cancer cell growth.

Results from studies using a solid matrix adsorbed with conditioned media indicated that non-dialyzable factor(s)

from bone fibroblast conditioned media samples alone could indeed induce LNCaP growth in vivo. This is the first demonstration that LNCaP tumor growth in vivo can be initiated by specific soluble growth factors derived from fibroblast cells. These results underscore the importance of growth factors in prostate cancer growth and progression.

Figure 11:
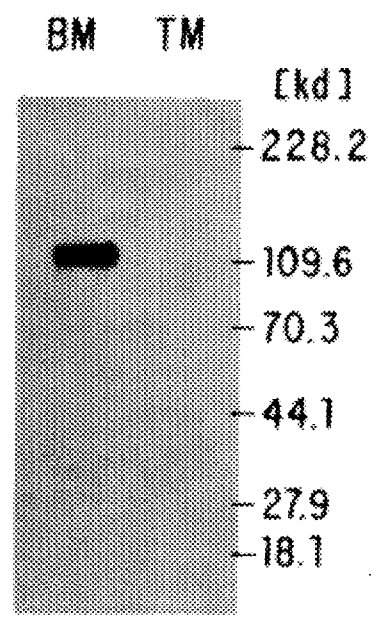
FIG. 11. Identification of a human growth factor polypeptide with an apparent molecular weight on SDS/PAGE of approximately 157 kD. This polypeptide, present within human bone marrow, is identified by its reactivity with the mAb MS 329 in Western blot analyses. BM, bone sample; TM, control media sample. The $M_r$s of the molecular weight standards are indicated to the left.

In further purifying the growth factors, by employing heparin sepharose chromatography, it was determined that the substantially purified fraction contained novel polypeptides with apparent molecular weights on SDS/PAGE of: 227, 223, 218, 157, 90, 80, 48, and 20 kD. These polypeptides were found to be distinct from bFGF by a number of criteria including differential elution from heparin sepharose columns and distinct immunoreactivity. The presence of the novel 157 kD polypeptide within the active fractions was not initially detected, presumably as it was masked by an irrelevant and inactive polypeptide also present in the control media. Its presence was shown following the generation of an anti-growth factor mAb, MS 329, which reacts with a 157 kD protein which is present in the active fractions, but absent from the control media (FIG. 11).

Skeletal tissues are known to produce various growth factors (Canalis et al., 1988; Wergedal et al., 1986; Sampath et al., 1986; Globus et al., 1989; Hauschka et al., 1986) including bFGF (Globus et al., 1989). Osteoblasts are the principal source of synthesis and deposition of bone matrix and the site where bFGF is stored and mediates its mitogenic activity (Globus et al., 1989; Hauschka et al., 1986). bFGF promotes LNCaP cell growth, and may also act in a paracrine fashion to stimulate metastatic cancer cell growth (Lu et al., 1989; Ensoli et al., 1989), but bFGF itself does not appear to be an active component of the growth factors disclosed herein. However, as anti-bFGF antibodies inhibited the bone fibroblast growth factor stimulatory action on prostate epithelial cells, albeit only slightly, the possibility remains that a bFGF-like protein may be responsible, in part, for the growth factor activity which stimulates prostate cell growth in vivo and in vitro.

EXAMPLE 1

Acceleration of Human Prostate Cancer Cell Growth In vitro and In Vivo by Factors Produced by Prostate and Bone Fibroblasts Materials and Methods 1. Cell Lines and Cell Culture.

LNCaP cells, passage 29, were obtained from Dr. Gary Miller (University of Colorado, Denver, Colo.) and grown in RPMI 1640 (Irvine Scientific, Santa Anna, Calif.) with 10% fetal bovine serum (FBS). Phenotypically, the cells resembled parental lines as evidenced by the results of karyotypic analysis and androgen receptor analysis (see below).

The six nontumorigenic mesenchymal cell lines analyzed in this study are as follows: a fetal urogenital sinus mesenchyme-derived cell line (rUGM) from 18-day old Noble rat fetuses, developed as described by Chung et al., 1984. rUGM cells were maintained in DMEM (Gibco Laboratories, Grand Island, N.Y.), 5% calf serum (CS), and passages 14–16 were used. A human bone fibroblast cell line, MS, derived from an osteogenic sarcoma, was established by Dr. A. Y. Wang (The University of Texas M. D. Anderson Cancer Center, Houston, Tex.). MS cells were maintained in T-medium (80% DMEM, 20% F12K [Irvine Scientific], 3 g/l NaHCO$_3$, 100 µ/ml penicillin G, 100 µg/ml streptomycin, 5 µg/ml insulin, 13.6 pg/ml triiodothyronine, 5 µg/ml transferrin, 0.25 µg/ml biotin, and 25 µg/ml adenine) with 5% FBS; passages 29–33 were used. A rat prostatic fibroblast line, NbF-1, was established from normal Noble rat ventral prostate gland as described previously (Chang & Chung, 1989). NbF-1 cells were maintained in DMEM and 5% CS and nontumorigenic passages 18–22 were used. Normal adult human lung fibroblasts, CCD16 (American Tissue Culture Catalogue CCL 204), were supplied by Dr. J. Roth (Dept. of Thoracic Surgery, UT M.D. Anderson Cancer Center, Houston, Tex.), and passages 14–16 were used. NIH-3T3 cells (ATCC #6587), derived from embryonic mouse tissue, were supplied by Dr. D. Becker (UT M. D. Anderson Cancer Center, Houston, Tex.) and maintained in DMEM with 5% CS. Normal rat kidney (NRK) fibroblasts (ATTC #6509) were grown in DMEM with 5% CS and passages 10–12 were used.

Conditioned media from LNCaP and all 6 fibroblast cell lines was collected and prepared as follows: Cells were cultured in 150 mm tissue culture dishes (Falcon, Becton Dickinson Laboratories, Lincoln Park, N.J.) with T-medium, 2% TCM, a serum-free defined media supplement (Celox Co., Minnetonka, Minn.), and 1% FBS until 60–70% confluent, washed with PBS/EDTA and changed to serum-free T-medium containing 2% TCM only. After 48 hours, the conditioned media was removed, filtered through a 0.2 µm filter (Nalge Co., Rochester, N.Y.), and 0.1 mM phenylmethyl-sulfonylfloride (PMSF, Sigma) was added. Protein concentrations in the conditioned media were determined using a protein assay (Bio-Rad Laboratories, Richmond, Calif.), and ranged from 70–100% of control (T-medium and 2% TCM; 1.3 mg/ml). The conditioned media was dialyzed at 4° C. against distilled water containing 0.1 mM PMSF using Spectra/Por 3 dialysis membranes ($M_r$>3500 dalton, PGC Scientifics, Gaithersburg, Md.) for 96 hours, changing the water after 48 hours. The samples were lyophilized to dryness and reconstituted in T-medium to ten times concentration (10×), filtered, and diluted to the desired working concentration (0.1 to 2×) with T-medium containing 2% TCM.

2. Assessment of in vivo Tumor Growth.

To determine the ability of specific fibroblasts to elicit LNCaP growth in vivo, 6–8 wk old athymic nude mice (BALB/c strain, Charles River Laboratory, Wilmington, Mass.) of both sexes were co-inoculated subcutaneously with 1×10$^6$ LNCaP cells and 1×10$^6$ of one of the 6 fibroblast cell lines described above. Up to 5×10$^6$ LNCaP cells and 2×10$^6$ of each of the fibroblast cell lines were injected alone as controls to assess their tumorigenicity. The cells were suspended in 0.1 ml of RPMI 1640 with 10% FBS prior to injection and inoculated via a 27 gauge needle. Tumors were measured twice weekly and their volumes were calculated by the formula L×W×H×0.5236 (Janek et al., 1975). At the time of sacrifice, sternotomy was performed and a cardiac puncture was carried out to obtain serum for PSA analysis. Tumors were excised, weighed, and subjected to various morphological and biochemical analyses (see below).

Further studies were performed to determine whether LNCaP tumor growth in vivo could be affected by soluble growth factors alone. LNCaP cells were injected along with a Gelfoam preparation (Upjohn, Kalamazoo, Mich.), adsorbed with type IV collagen (Collaborative Research, Bedford, Mass.), endothelial cell derived growth factor (ECGF) (Collaborative Research), and ten times concentrated rUGM or MS conditioned media. This novel matrix system was developed through modification of a previously described procedure (Thompson et al., 1988) and serves as a reservoir for delivery of biologically active factors in vivo.

ECGF was chosen as a marker of physiologic response to determine whether it could retain its biologic activity during this procedure, and whether this angiogenesis alone would be sufficient to promote tumor formation. rUGM and MS conditioned media were used because these cells could induce LNCaP growth in vivo. Basic fibroblast growth factor (bFGF, Collaborative Research) was also used because of its mitogenic effect on LNCaP cells in vitro (see below).

Under sterile conditions, Gelfoam, a solid gelatin sponge, was pre-soaked with 100 µg/ml collagen IV for 12 hours at 4° C., followed by either 1 µg/ml ECGF, bFGF, or ten times concentrated stromal conditioned media for 1 hour. The Gelfoam was then minced using a polytron to allow subcutaneous inoculation via an 18 gauge needle. Following subcutaneous injection of 0.1 ml Gelfoam, the same site was injected with $2\times10^6$ LNCaP cells using a 27 gauge needle. For controls, $2\times10^6$ LNCaP cells were inoculated with Gelfoam and collagen IV, with or without ECGF. Tumor incidence and size was monitored as described above.

3. Histology and Immunohistochemistry.

For routine histology, specimens were fixed in 10% neutral buffered formalin and embedded in paraffin. Eight micron fixed sections were cut and stained with hematoxylin and eosin (H&E). For immunohistochemical studies, specimens were deparaffinized with xylene, rehydrated with 70% ethanol, and treated with 0.1% trypsin for 10 min at 37° C. Sections were then incubated with monoclonal antibodies prepared against cytokeratin, PSA, or prostatic acid phosphatase (PAP) (Biogenex, Dublin, Calif.). An avidin-biotin complex method was used with all specimens using fast red TR or AEC as chromogens (Biogenex). Slides were counterstained with aqueous hematoxylin and mounted with glycerol for visual inspection and photography.

4. Determination of Serum PSA Values.

Animals were killed by cardiac puncture under methoxyfluorane anesthesia. Blood was allowed to clot at 37° C. and centrifuged, and the serum was stored at -20° C. PSA values were determined using a dual reactive enzymatic immunoassay kit with a lower limit of sensitivity of 0.4 ng/ml (Hybritech Inc., San Diego, Calif.).

5. DNA Isolation and Southern Blot Analysis.

Tissue DNA was isolated from tumors as described by Davis (1986). DNA concentration was determined with a spectrophotometer. DNA specimens were applied to Zetaprobe membranes (Bio-Rad) then baked at 80° C. for 90 minutes prior to hybridization with a $^{32}$P-labeled human Alu repetitive sequences probe (Oncor, Gaithersburg, Md.).

6. RNA Isolation and Northern Blot Analysis.

Total cellular RNA was prepared from frozen tissues by the 4 M guanidinium thiocyanate extraction method (Chomcjymski & Sacchi, 1987). Typical yields of total cellular RNA were about 300 µg/200 mg tissue as quantified spectrophotometrically using 40 µg RNA/$A_{260}$ unit. RNA was denatured in 50% formamide/18% formaldehyde at 55° C. and fractionated by electrophoresis in a 0.9% denaturing formaldehyde agarose gel. Samples were transferred onto a Zetaprobe membrane (Bio-Rad) by capillary method, and the membrane was then baked for 2 hours at 80° C. Following this, the membrane was prehybridized in the presence of 1 M NaCl, 10% dextran sulfate, 1% SDS, and 200 µg/ml salmon sperm DNA for at least 2 hours at 65° C. Hybridization was carried out at 65° C. overnight with a random-primer-labeled probe as indicated. The cDNA probe for PSA was obtained from Dr. D. Tindall (Mayo Clinic, Rochester, Minn.) (Lundwall & Lilja, 1987). Finally, the membrane was washed under high stringency conditions (0.5×SSC, 1% SDS at 65° C.). Autoradiograms were prepared by exposing Kodak X-Omat AR film to the membrane at -80° C. with intensifying screens.

7. Mitogenic Assays.

To determine the mitogenic activity of androgens (testosterone and dihydrotestosterone, Sigma) and conditioned media prepared from various types of fibroblasts on the growth of human LNCaP cells in vitro, we used a 96-well assay based on the uptake and elution of crystal violet dye by the cells in each well (Gillies et al., 1987; Kanamarus & Yoshida, 1989). Various defined growth factors, including basic fibroblast growth factor (bFGF), transforming growth factors alpha and beta (TGFα, TGFβ) and epidermal growth factor (EGF) (Collaborative Research) were also tested.

Using 96 well plates, 3,000 LNCaP, 500 MS, or 200 rUGM cells were plated per well (Falcon) in T-medium containing 1% charcoal stripped CS and 2% TCM. Twenty-four hours later, the cells were downshifted to serum-free condition (see above) with various concentrations of androgens, growth factors, or conditioned media. To avoid stripping poorly adherent LNCaP cells with each media change, media was partially removed by gentle suction and 100 µl of fresh media was added in 50 µl aliquots. The medium was changed every 2 days; 7-10 days later the cells were fixed in 1% glutararalydehyde (Sigma), and stained with 0.5% crystal violet (Sigma). Plates were washed, air-dried, and the dye was eluted with 100 µl Sorensen's solution (9 mg trisodium citrate in 305 ml distilled $H_2O$, 195 ml of 0.1N HCl, and 500 ml 90% ethanol). The absorbance of each well was measured by a Titertek Multiskan TCC/340 (Flow Laboratories, McLean, Va.) at 560 nm. Control experiments demonstrated that absorbance is directly proportional to the number of cells in each well.

8. Androgen Receptor Assays.

Whole cell androgen receptor assays were performed as described previously by Guthrie et al. (Guthrie et al., 1990), with the following modifications. LNCaP cells were plated in T-medium plus 5% FBS in 6 well plates (Falcon) and downshifted to 0.4% charcoal-stripped calf serum 24 hours preceding the assay. Just prior to beginning the assay, this medium was removed and cells were washed twice with PBS/EDTA, and T-medium with various dilutions of $^3$H-R1881 (methyltrienolone 81.8 Ci/mmol, DuPont Co., Wilmington, Del.) was added to appropriate wells. In some wells, unlabeled R1881 (200-fold of [$^3$H-R1881]) was added to determine the extent of nonspecific binding. Following a 90 minute incubation at 37° C., the media was removed, cells were washed with ice cold PBS/EDTA, and 1 ml of 100% ethanol was added to each well. A 500 µl aliquot was added to a scintillation vial and counted with a scintillation counter (Beckman Instruments, Inc., Houston, Tex.).

Results

1. Effect of Co-inoculated Fibroblasts on LNCaP Tumor Growth.

The incidence of tumor formation in mice co-inoculated with LNCaP cells and various types of fibroblasts was compared (Table I). The observation period for all injections was 3 months. LNCaP and all fibroblast cell lines were found to be nontumorigenic (0/20) with injections of up to $5\times10^6$ or $2\times10^6$ cells, respectively. No significant sex differences in tumor formation were observed in hosts coinoculated with LNCaP and rUGM cells, with an overall tumor incidence of 61% for males and 50% for females. The average latency period for measurable tumor growth was 42 days in male and 45 days in female hosts. No difference in tumor volume or latency period was observed by increasing the rUGM inoculum from 1×10$^5$ to 1×10$^6$ cells. Mean tumor volume was 322±106 mm$^3$. No sex differences in the incidence of tumor formation was observed in hosts coinoculated with LNCaP and 3T3 cells (67%, mean tumor volume 420 mm$^3$). In contrast, marked sex differences in tumor induction were observed with coinoculation of LNCaP and human bone (MS) or LNCaP and rat prostatic (NbF-1) fibroblasts, as these tumors formed only in male hosts (62% and 17%, respectively). Mean tumor volume for LNCaP/MS and LNCaP/NbF1 tumors was 238±74 mm$^3$ and 72±52 mm$^3$, respectively. Lung CCD16 and NRK fibroblasts did not induce chimeric tumor growth in either sex. The histomorphology and relative content of LNCaP cells in the various fibroblast-induced tumors differed markedly, as characterized below.

TABLE 1

FIBROBLAST SPECIFICITY IN INDUCING HUMAN PROSTATE CANCER GROWTH

| Fibroblast | Host | Incidence of tumor formation | Histomorphology of tumors | |
|---|---|---|---|---|
| | | | Carcinosarcoma | Sarcoma |
| MS | Male | 8/13 (62%) | 8/13* (62%) | 0/13 (0%) |
| | Female | 0/10 (0%) | | |
| rUGM | Male | 31/51 (61%) | 16/51 (31%) | 15/51 (30%) |
| | Female | 18/36 (50%) | 2/36 (6%) | 16/36 (44%) |
| NbF-1 | Male | 3/18 (17%) | 3/18 (17%) | 0/18 (0%) |
| | Female | 0/10 (0%) | | |
| CCD16 | Male | 0/20 (0%) | | |
| | Female | 0/6 (0%) | | |
| NRK | Male | 0/20 (0%) | | |
| | Female | 0/10 (0%) | | |

*All carcinomas with no sarcomatous component

In further studies of this kind, only nonirradiated human bone stromal (MS) cells were found to be active in promoting LNCaP tumor formation (Table 2).

TABLE 2

| Fibroblast | LNCaP Cell | Incidence of tumor formation* |
|---|---|---|
| None | 2 × 10$^6$ | 0/6 (0%) |
| MS 1 × 10$^6$ (nonirradiated) | 1 × 10$^6$ | 15/17 (88%) |
| MS 1 × 10$^6$** (irradiated) | 1 × 10$^6$ | 0/8 (0%) |
| CCD16 1 × 10$^6$ | 1 × 10$^6$ | 0/6 (0%) |

*Incidence of tumor formation was recorded 32–54 days after inoculation
**The cells were irradiated with 40 Gy before coinoculation with LNCaP Cells 2. Characterization of the Chimeric Tumors.

Figure 1B:
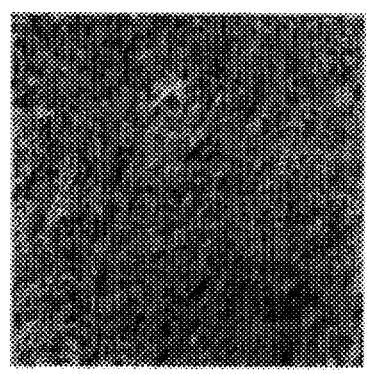
Figure 1C:
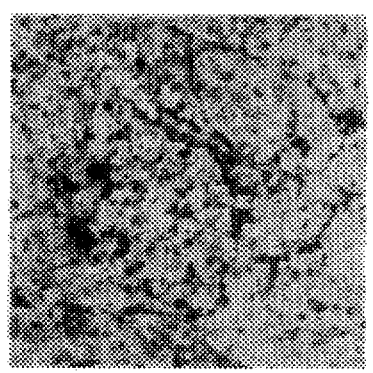

Chimeric tumors were characterized histomorphologically, immunohistochemically, and biochemically. A difference in histomorphology of LNCaP/rUGM chimeric tumors was noted between males and females: in males, 51% of tumors (or 31% of inoculation sites) were carcinosarcomas, with a predominantly epithelioid component separated by strips of mesenchymal cells (FIG. 1a), while 89% (16/18) of the tumors in females were pure sarcomas (FIG. 1b). MS bone fibroblasts were found to be the most potent inducer of LNCaP tumor formation. All tumors were carcinomas composed of sheets of poorly differentiated epithelial cells with minimal mesenchymal cells and formed at 62% of inoculated sites in male hosts (FIG. 1c); no tumors formed in female hosts. NbF-1 cells were also capable of inducing LNCaP tumor growth in male hosts, but not as well as the MS or rUGM cells; three carcinomas formed from 18 inoculations (17%). LNCaP/3T3 tumors, however, were all sarcomas with no epithelial component. No tumors formed with coinoculation of LNCaP with human lung CCD16 or NRK fibroblasts.

Figure 1D:
Figure 1E:
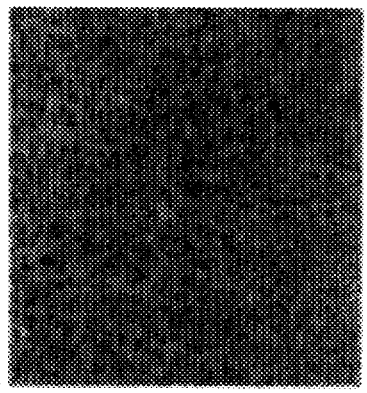
Figure 1F:
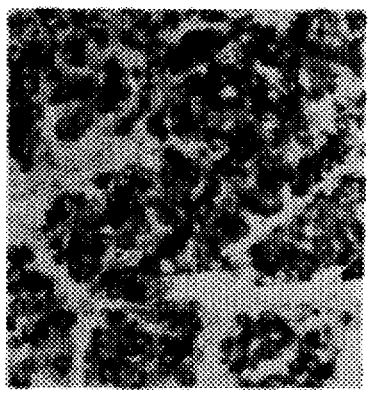

The prostatic origin of the epithelial cells participating in the MS-, rUGM-, and NbF-induced tumor formation in male hosts was confirmed with immunohistochemical staining procedures using monoclonal antibodies directed against PSA, PAP, and cytokeratin. The epithelial component of these tumors stained intensely positive for PSA using fast red TR as the chromogen (FIG. 1d; FIG. 1f) with no staining of the associated stromal component. The epithelial component of these tumors also stained positive for PAP and cytokeratin, but in an irregular and scattered manner compared to PSA. In contrast, sarcomas arising from LNCaP/rUGM inoculations in females and LNCaP/3T3 inoculations in both males and females stained negatively for PSA (FIG. 1e), PAP, and cytokeratin.

Figure 2A:
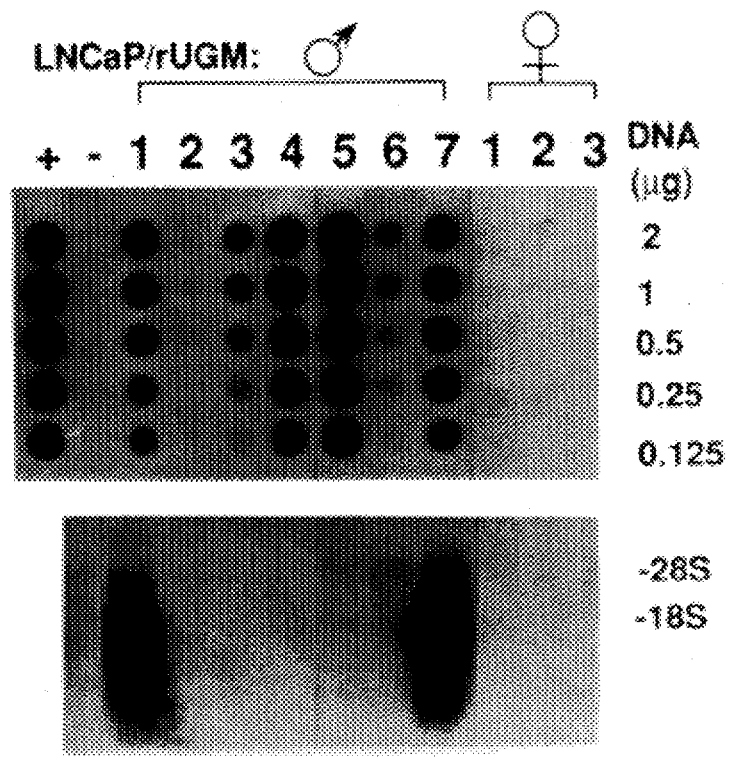
FIGS. 2a and 2b. Southern and Northern analysis of fibroblast-induced LNCaP chimeric tumors. Portions of tumors removed at the time of sacrifice were processed separately for DNA and RNA isolation as described in the detailed examples. Controls consisted of human bladder cancer (+) and rUGM (-) cell DNA. Various concentrations of DNA were loaded and probed for repetitive Alu sequences to identify human cells. RNA, 20 μg, was loaded and probed with a complementary DNA probe for PSA. (a), Southern dot blot of LNCaP/rUGM tumors demonstrating variably positive Alu in 6 or 7 tumors from male hosts (lanes 1–7) and 0 or 3 tumors from female hosts (lanes 1–3). Northern analysis of corresponding tumors (a, bottom) demonstrates PSA expression only in tumors from male hosts. PSA expression did not correlate with alu expression, likely resulting from varied tissue selection from a heterogenous tumor. (b), Southern analysis of LNCaP/3T3 tumors reveals no human component in these tumors (lanes a–e), while all LNCaP/MS tumors were positive for Alu (lanes f–j). Northern analysis of LNCaP/MS tumors (b, bottom) demonstrates that all are strongly positive for PSA.
Figure 2B:
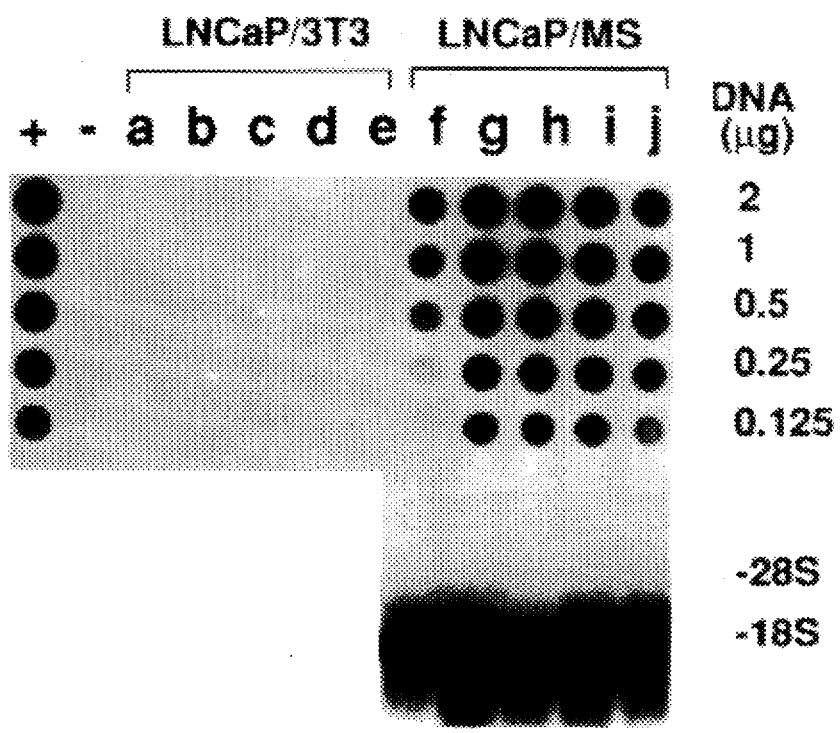

Biochemical characterization using Northern and Southern hybridization techniques corroborated the histologic findings to confirm the human prostatic origin of the epithelial component of the chimeric tumors (FIG. 2). The LNCaP/rUGM tumors in male hosts contained a predominantly human component as manifested by the presence of Alu-sequences in 6 (2 weakly) of 7 tumors examined, compared to none in female tumors (FIG. 2a). PSA expression was more variable in these tumors and did not correlate consistently with the histomorphologic and Southern dot-blot analysis, likely because of different sampling from a heterogenous carcinosarcoma. All LNCaP/MS tumors were strongly positive for PSA expression and human-specific Alu sequences on Northern and Southern analysis, respectively (FIG. 2b). None of the LNCaP/3T3 tumors that formed had any human prostate component (FIG. 2b).

3. Serum PSA Levels.

Figure 3A:
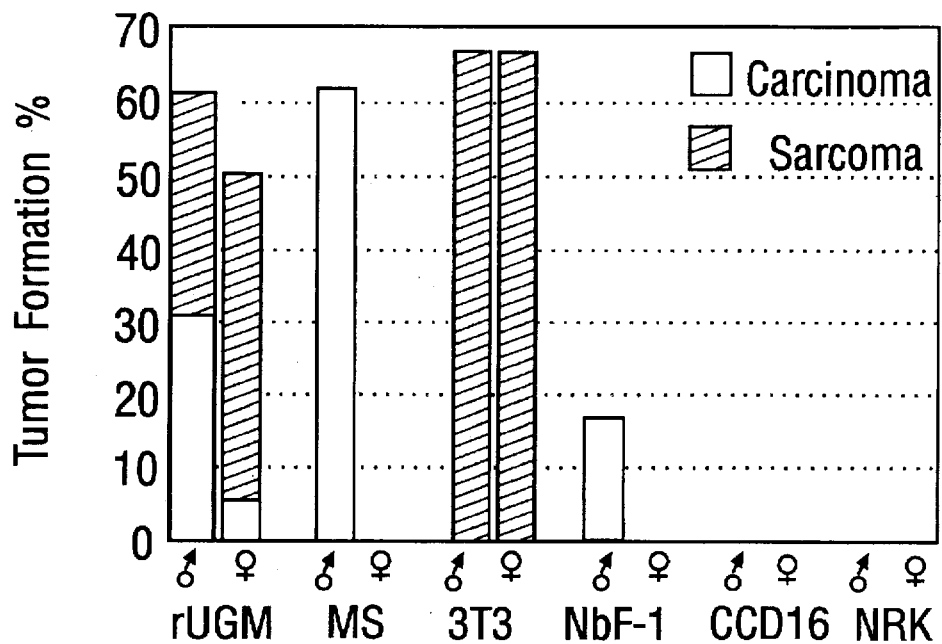
FIGS. 3a and 3b. Differences in serum PSA levels (ng/ml) in animals with various LNCaP chimeric tumors paralleled their differences in histomorphology. Mice bearing tumors characterized as carcinosarcomas (LNCaP/rUGM) or carcinomas (LNCaP/MS or LNCaP/NbF-1) (a) had elevated serum PSA levels (b), while mice bearing sarcomas or no tumors had undetectable serum PSA levels (<0.3 ng/ml). MS bone fibroblasts were the most reliable inducer of LNCaP carcinoma formation and resulted in the highest PSA levels, with a median of 68.1 ng/ml.
Figure 3B:
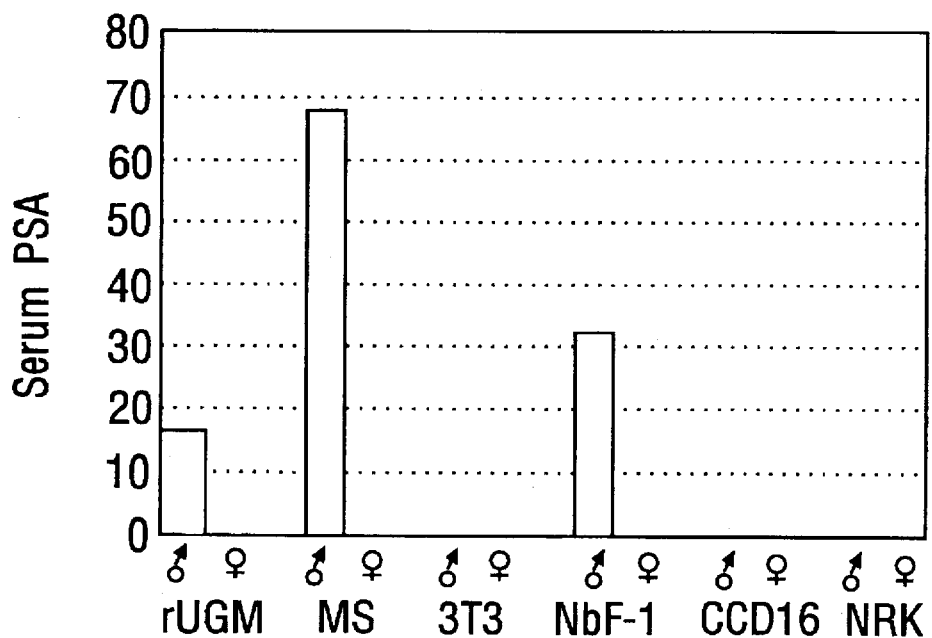

Sera from male and female mice bearing chimeric tumors were assayed for PSA using the Hybritech enzyme immunoassay. Four control males injected with human bladder transitional cell carcinoma cells (Stamey et al, 1987) had undetectable PSA levels, as anticipated, as PSA is a human prostate marker. Significant differences in median serum PSA values were observed among the different fibroblast-induced tumors as well as male and female hosts, paralleling differences in their histomorphology (FIG. 3). LNCaP/MS tumors were associated with consistently elevated serum PSA levels ranging from 25.1 ng/ml to 323 ng/ml, with a median of 68.1 ng/ml (n=6). Similarly, male hosts bearing LNCaP/NbF-1 tumors had elevated serum PSA (n=4). However, nontumor-bearing females with LNCaP/MS and LNCaP/NbF- 1 injections had undetectable serum PSA levels. Serum PSA values in males with LNCaP/rUGM tumors ranged from 0.4 to 348 ng/ml with a median of 16.1 ng/ml; 11 of 12 males had detectable levels and 3 had levels >100 ng/ml. In all but one of the 8 females with LNCaP/rUGM tumors, serum PSA was undetectable. All animals with LNCaP/3T3 tumors, as well as those inoculated with LNCaP/CCD16 or LNCaP/NRK cells, had undetectable serum PSA levels.

4. LNCaP Androgen Sensitivity and Androgen Receptor Content.

Figure 4A:
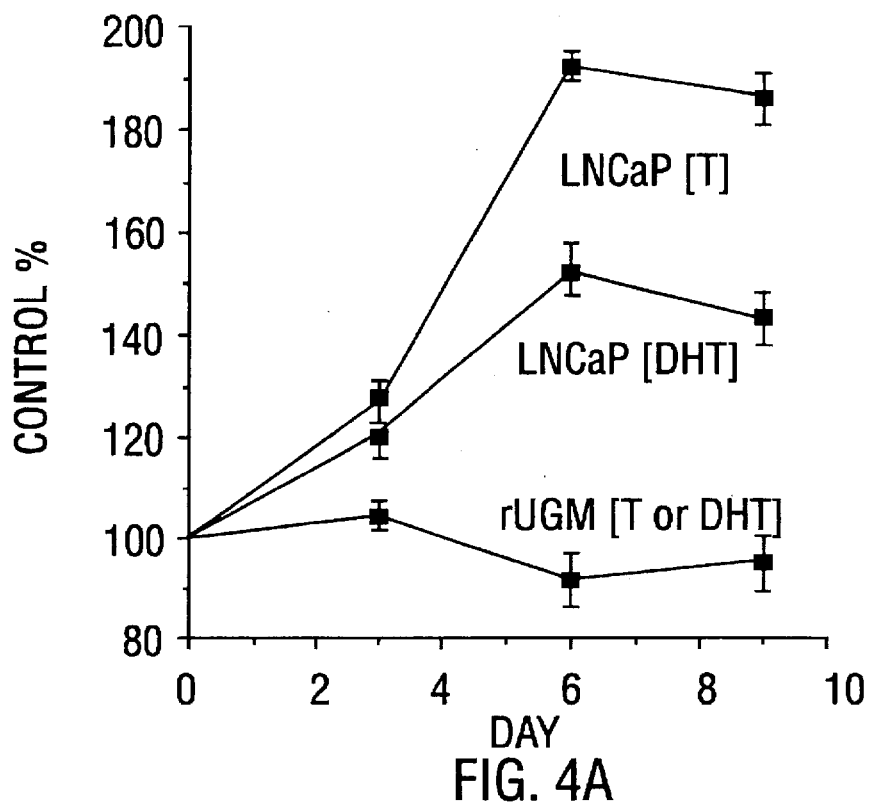
FIGS. 4a and 4b. LNCaP cells are androgen sensitive in vitro. (a), LNCaP cells were stimulated in vitro by androgens with a 182 and 142% increase in cell growth with 1.0 nM testosterone (T) and 0.1 nM dihydrotestosterone (DHT), respectively. No mitogenic response was observed for rUGM cells using androgens in concentrations ranging from 0.1 to 100 nM. (b), androgen receptor assays demonstrated the presence of a substantial amount ($B_{max}$=332 fmol/mg protein) of high-affinity ($K_d$=0.22 nM) androgen receptors in LNCaP cells. Points, averages of 6 replicated determinations from 3 separate experiments; bars, SE ranging from 3–9%.
Figure 4B:
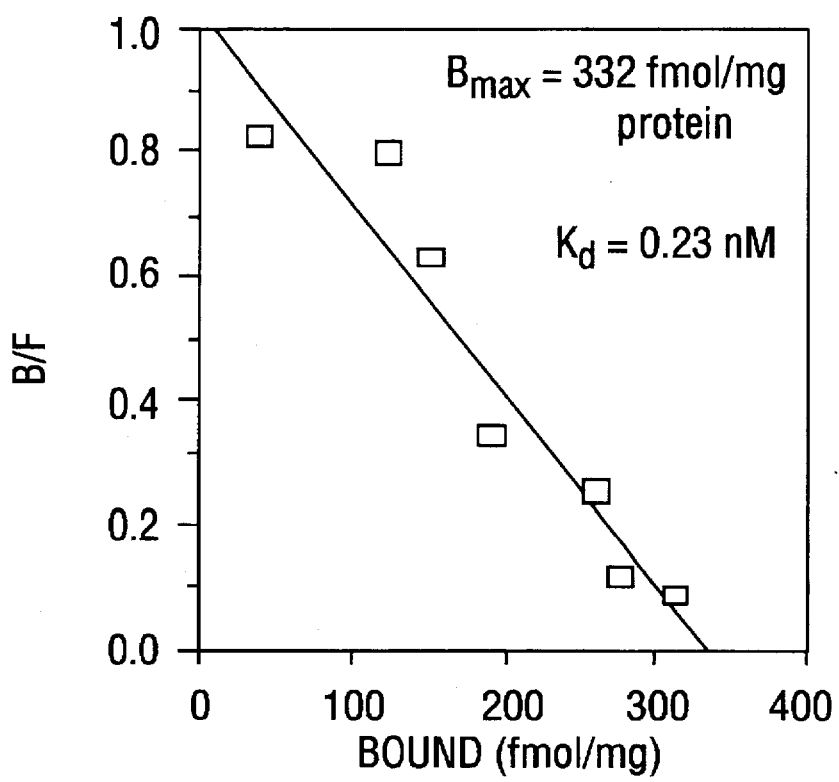

To determine whether the LNCaP cell line was indeed androgen-sensitive, the in vitro mitogenic effects of testosterone and DHT in serum-free and chemically-defined medium were evaluated. Peak responses were seen with $5 \times 10^{-10}$ M testosterone and $1 \times 10^{-10}$ M DHT, producing 62% and 43% increases, respectively, in cell number over 9 days when compared to controls grown in serum- and hormone-free media (FIG. 4a). Whole cell androgen receptor assays revealed the presence of a substantial number of high affinity androgen receptors ($K_d$=0.23 nM; $B_{max}$=332 fmol/mg protein, FIG. 4b).

5. Effect of Defined Growth Factors on LNCaP Cells in vitro.

Figure 5A:
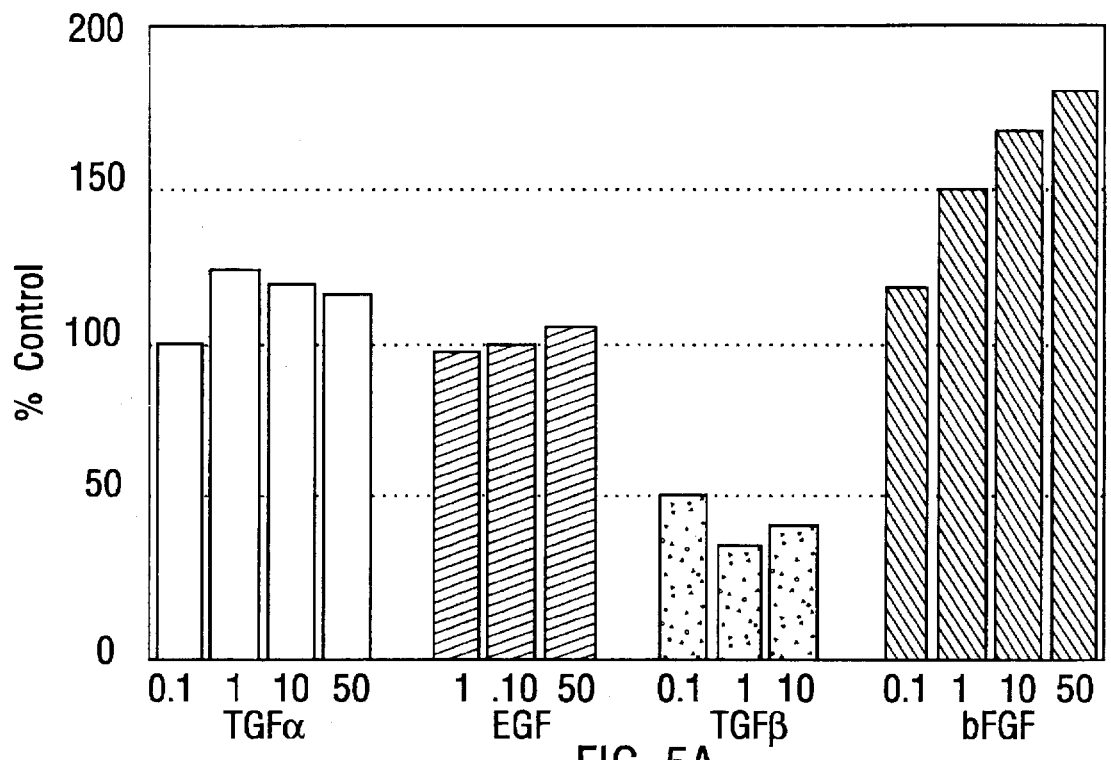
FIGS. 5a and 5b. Effect of defined growth factors on LNCaP cell growth in vitro. The growth of LNCaP cells are stimulated in vitro by bFGF in a concentration-dependent manner (a), producing a 180% increase in cell number over 9 days. Both TGFα and EGF had no significant effect on LNCaP growth in vitro using concentrations from 0.1 to 50 ng/ml. A 50% reduction in LNCaP cell growth was produced by 0.1 ng/ml TGFβ (b). Points, averages of 6 replicated determinations from 3 separate experiments; bars, SE ranging from 3–9%.
Figure 5B:
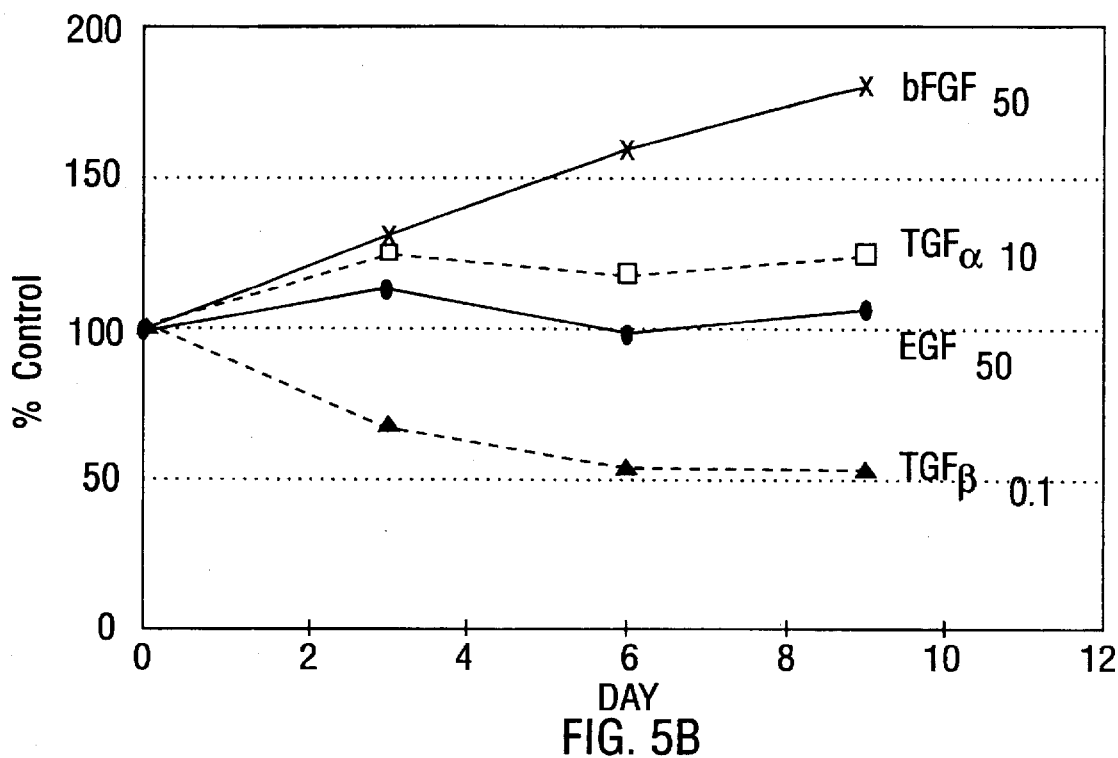

To identify possible mitogens involved in LNCaP cell growth, the dose-response relationship between LNCaP cells and bFGF, EGF, TGFα, and TGFβ was investigated. Using concentrations ranging from 0.1 to 50 ng/ml, bFGF stimulated LNCaP cell growth 180% in a concentration-dependent manner compared to cells grown in serum-free media alone (FIG. 5a). Minimal increases in cell number compared to controls were seen with EGF and TGFα over a wide range of concentrations. TGFβ, at 1 ng/ml, inhibited LNCaP cell growth by 70%. Time course studies also revealed that bFGF (50 ng/ml) stimulated LNCaP cell growth in a linear fashion during a 9-day observation period (FIG. 5b).

6. Effect of Fibroblast-Conditioned Medium on the Growth of LNCaP Cells in vitro.

Figure 6A:
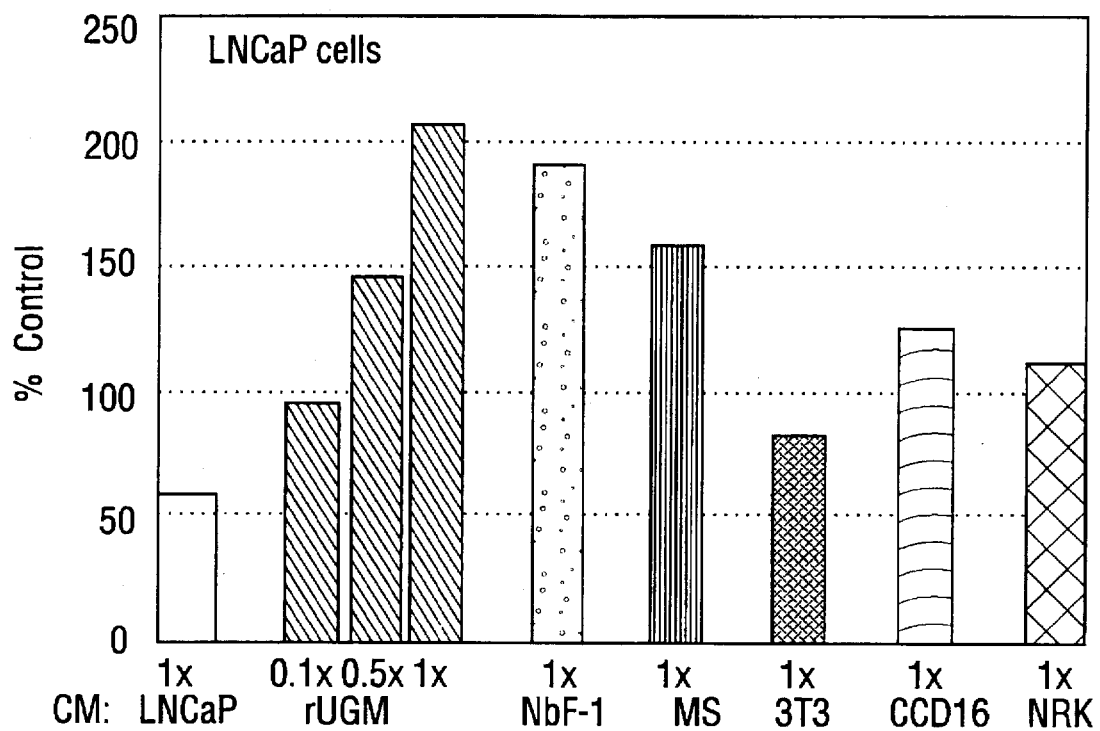
FIGS. 6a and 6b. Stimulation of LNCaP cell growth in vitro by prostate- and bone-derived conditioned media. (a), LNCaP cells are stimulated up to 210% in a concentration-dependent manner from 0.1- to 1.0-fold by rUGM conditioned media and are also stimulated by NbF-1 and MS conditioned media, but not by 3T3, CCD16, or NRK conditioned media. (b), a bidirectional paracrine-mediated stimulatory pathway exists between LNCaP cells and rUGM and MS fibroblasts. rUGM cells are stimulated up to 400% in a concentration-dependent manner from 0.1- to 2-fold by LNCaP conditioned media and also less so by NbF-1, MS, 3T3, and CCD16 conditioned media. No autocrine growth loop was demonstrated as evidenced by lack of stimulation of LNCaP conditioned media on LNCaP cells or rUGM conditioned media on rUGM cells. Columns, averages of 6 replicated determinations from 3 separate experiments; bars, SE ranging from 2–7%.
Figure 6B:
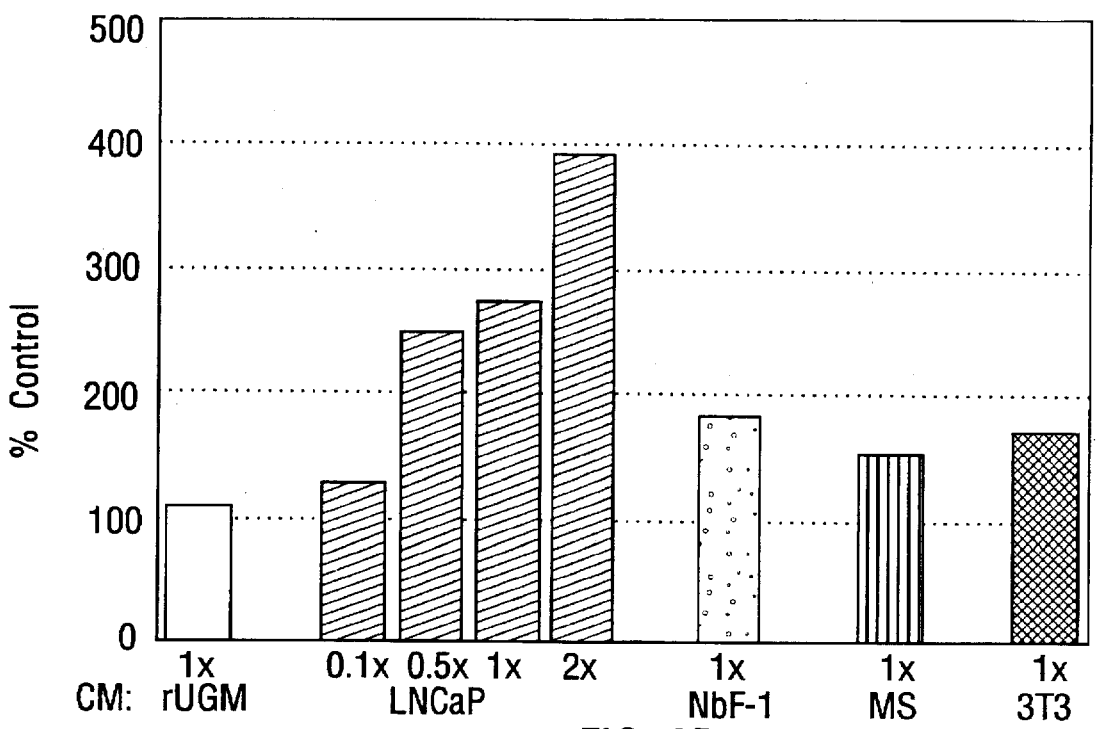

To determine whether the in vivo fibroblast specificity in inducing LNCaP growth could be explained by specific soluble growth factors produced by the fibroblasts, the mitogenic activity of conditioned media from MS, rUGM, NbF-1, 3T3, CCD16, and NRK cells on LNCaP growth in vitro was compared. The conditioned media from MS, rUGM, and NbF-1 cells stimulated LNCaP cell growth up to 210% compared to controls (FIG. 6a), whereas 3T3, CCD16, and NRK conditioned media were ineffective. This paracrine effect was observed to be bidirectional, as LNCaP conditioned media stimulated rUGM cell growth up to 275% (FIG. 6b) and MS cell growth 225%. The bidirectional paracrine stimulation between LNCaP and rUGM or MS cells in vitro is dependent on the concentration of conditioned media. No autocrine stimulatory effect was observed on exposing LNCaP, rUGM, or MS cells to their own conditioned media.

7. Effect of MS- and rUGM-Conditioned Media and bFGF on LNCaP Growth in vivo.

Since MS- and rUGM-conditioned media and bFGF stimulated LNCaP cell growth in vitro, possible growth-promoting effects in vivo were examined following the coating of these growth factor onto a solid Gelfoam matrix. Control subcutaneous injections of Gelfoam with collagen IV plus ECGF with no coinoculated LNCaP cells was found to induce local neovascularization at 3 wk (FIG. 7b) illustrating that certain growth factors could maintain their biological activity when injected subcutaneously with this technique. Coinoculation of $2 \times 10^6$ LNCaP cells with Gelfoam adsorbed with collagen IV alone or with collagen IV and ECGF failed to induce LNCaP tumor formation.

However, when $2 \times 10^6$ LNCaP cells were inoculated with Gelfoam plus collagen IV adsorbed with either bFGF (1 µg/ml) or 10× concentrated conditioned media from rUGM or MS cells, LNCaP tumors formed at 60%, 50% and 38% of inoculated sites, respectively. Tumor latency, growth rate and size was similar, and did not differ from that of chimeric tumors induced by coinjecting LNCaP cells with rUGM or MS fibroblasts. Animals bearing LNCaP tumors had an elevated serum PSA (median 73 ng/ml) and the tumors were histologically carcinomas staining positive for PSA (FIG. 7c). The human prostatic origin of these tumors was confirmed with Southern dot-blot analysis for human Alu sequences and Northern analysis for PSA mRNA expression (FIG. 7d).

EXAMPLE 2

Isolation and Characterization of Growth-Promoting Factor(s) in the Conditioned Media of Cultured Human Bone Stromal Cells As shown in Example 1, section 7, accelerated LNCaP tumor growth still occurred in vivo when human bone stromal cells themselves were substituted by their conditioned media. Also, purified bFGF induced LNCaP tumor growth both in vitro and in vivo. These observations prompted further investigation of the properties of the conditioned media, and raised the possibility that bFGF itself may be the active component of the conditioned media.

Figure 8:
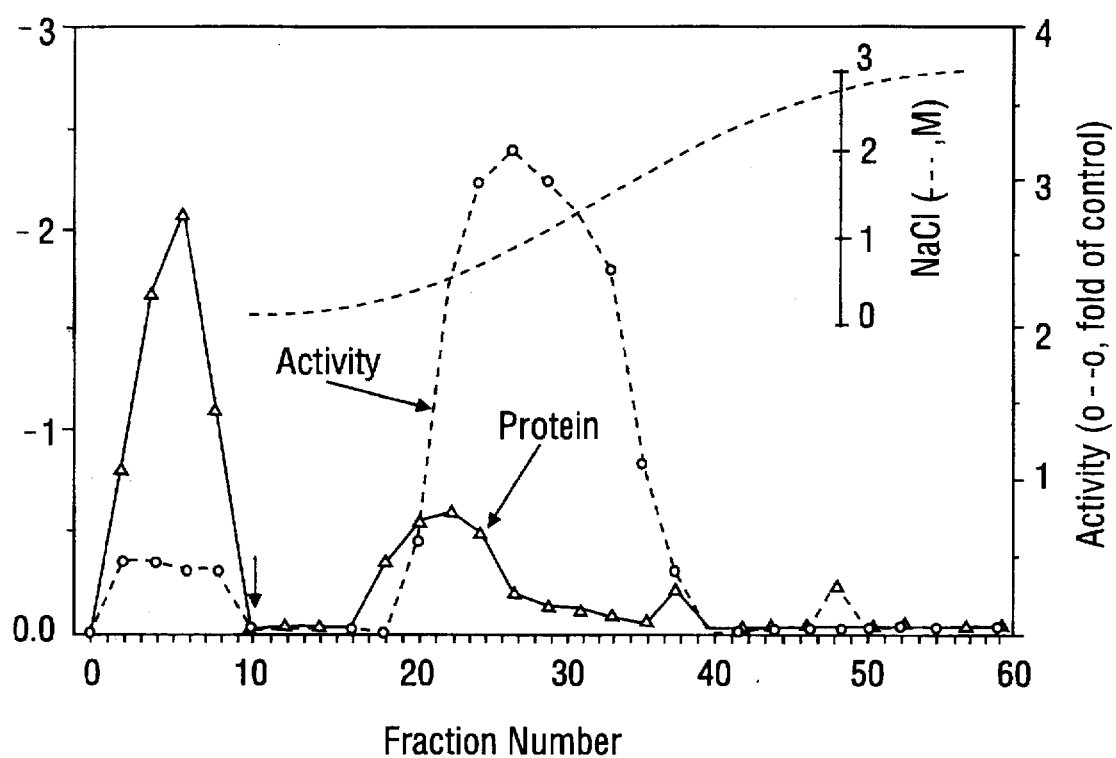
FIG. 8. Heparin affinity column chromatography of human bone stromal conditioned media. 560 mg total MS conditioned media protein was loaded onto the column. The column was washed with 10 mM Tris-HCl, 1 mM PMSF, pH 7.4, before eluting with a continuous salt gradient of 0 to 3 M NaCl. The tumor inducing activity was recovered prior to elution with 2 M NaCl.

The MS conditioned media was dialyzed prior to further purification and analysis. Firstly, a sample of conditioned media was subjected to affinity chromatography using a heparin sepharose column. The sample was loaded onto the column in the low salt-containing buffer 10 mM Tris/HCl, 1 mM PMSF, pH 7.4, to allow binding to the column, and the column was then washed with this buffer to remove any non-binding species. The components that bound to the column were then eluted using the above buffer containing an increasing gradient of NaCl, from 0–3 M. Following assays of the eluted material, it was determined that the peak of the active component(s) responsible for LNCaP tumor growth in vivo corresponded to the 1 M NaCl eluted fraction (FIG. 8). This is distinct from bFGF, which is known to elute at >2.0 M NaCl (Story et al., 1987). As can be clearly seen in FIG. 8, even the trailing edge of the activity peak eluted prior to exposure to 2 M NaCl.

Figure 9:
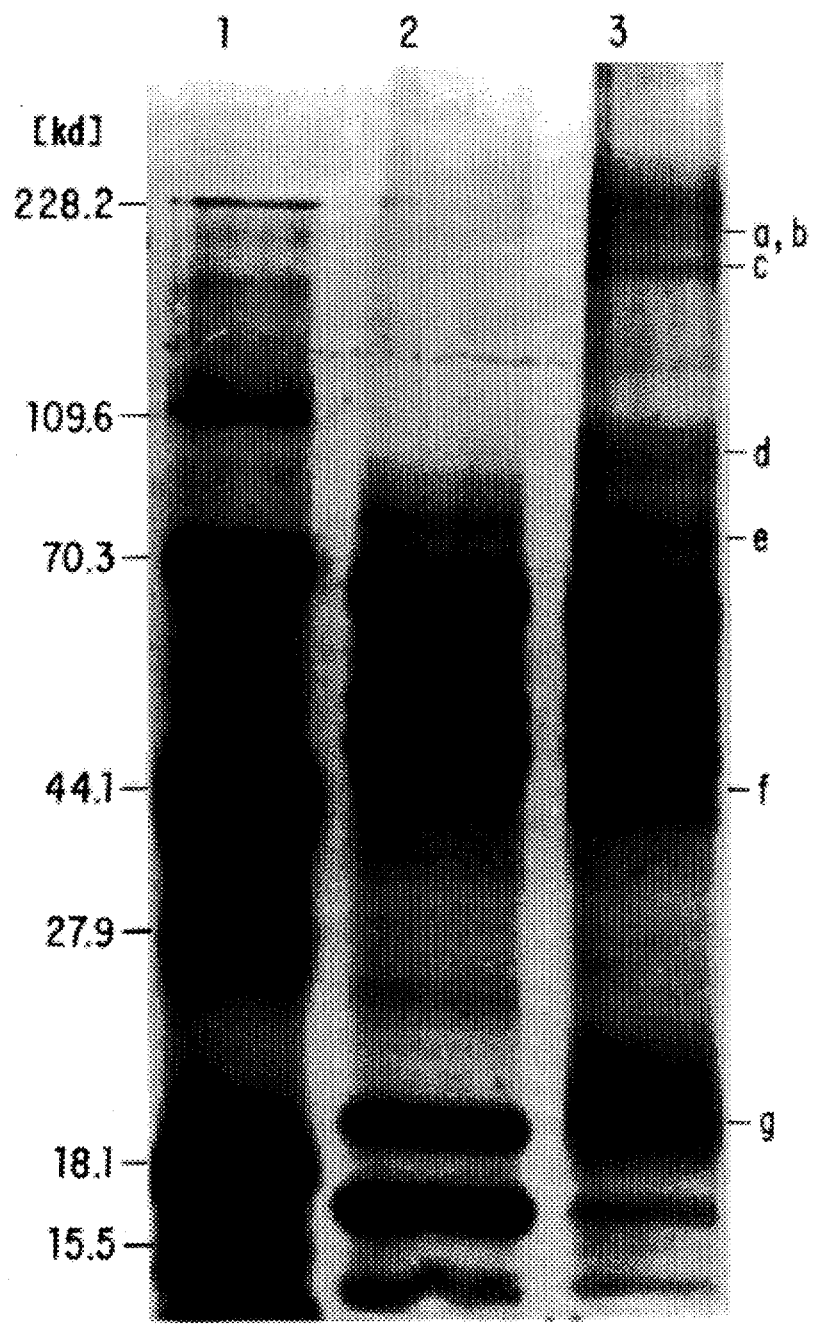
FIG. 9. SDS-PAGE analysis of the active fractions (1 M NaCl-eluted fractions) from heparin sepharose chromatography. Track 1, high-molecular weight markers; track 2, control media; track 3, active fractions.

The SDS/PAGE profile of this partially purified heparin sepharose-eluted growth factor preparation was then determined and compared to the control media (TCM). Following silver stain analysis of SDS gels, several distinct polypeptide bands in the $M_r$ range of 18 to 228 kDa were found to be present in this fraction, which were absent from the control (FIG. 9, track 3 vs. track 2).

The presence of a further novel 157 kD polypeptide within the active fractions was not initially detected, presumably as it was masked by an irrelevant and inactive polypeptide also present in the control media. Its presence was shown following the generation of an anti-growth factor mAb, MS 329, which reacted with a 157 kD protein present in the active fractions and absent from the control media (FIG. 11).

The activity of this fraction in stimulating prostatic cell growth and soft agar colony formation, and in inducing in vivo LNCaP tumor growth was investigated and compared to that of other fractions. The soft agar colony formation assay is a standard in vitro assay to test for transformed cells, as only such transformed cells can grow in soft agar. 0.6% (w/v) agar was placed into the bottom of each well on a 24 well plate, and each well was seeded with 2,000 NbE-1 cells. A feeder layer of 0.3 to 0.4% (w/v) agar, containing the potential growth factor substances to be analyzed, was then placed on top of the cells. The number of soft agar colonies formed was recorded 3 to 4 weeks after seeding. The active fractions (1 M eluates) from the column were found to be particularly active in both assays, whereas control media, the 2 M NaCl eluate, and similar fractions eluted by 1 M NaCl from 3T3 cell conditioned media, were found to be completely inactive (Table 3).

TABLE 3

| Condition | Incidence of Tumor Formation | Soft Agar Colony Formation |
|---|---|---|
| Gelfoam & Collagen IV | 0/6 (0%) | 4 ± 1.5 |
| +MS 1.0M NaCl Eluate | 9/12 (75%) | 121 ± 7.2 |
| +MS 2.0M NaCl Eluate | 0/24 (0%) | — |
| +3T3 1.0M NaCl Eluate | — | 2 ± 0.7 |
| +TCM 1.0M NaCl Eluate | 0/6 (0%) | 4 ± 0.7 |

The properties of the partially purified heparin sepaharose-eluted growth factor preparation were then further investigated. The mitogenic and tumor-forming activities were found to be trypsin and heat sensitive, but to be partly resistant to acid and reducing agent treatment (Table 4).

TABLE 4

| Condition | Remaining activity (%)* |
|---|---|
| None | 100 |
| Heat | |
| 70° C., 5 min | 66 ± 4 |
| 100° C., 5 min | 18 ± 3 |
| HCl, 1N | 52 ± 4 |
| Dithiothreitol (0.05M) | 63 ± 3 |
| Trypsin (10 ug/ml) | 0 |

*Defined by [$^3$H] thymidine incorporation into cellular DNA

Figure 10:
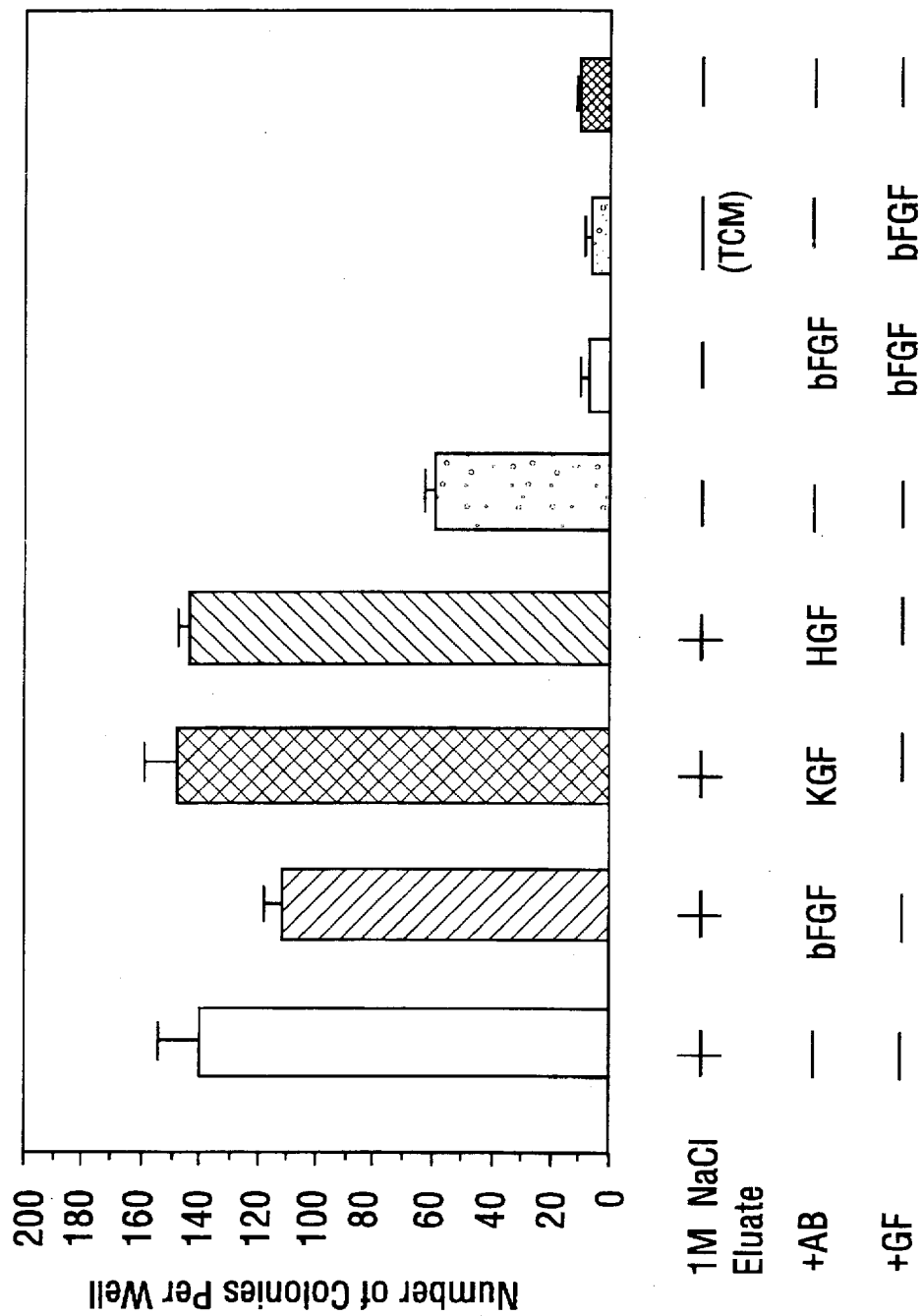
FIG. 10. Effect of various growth factors antibodies antagonizing the efficiency of soft agar colony formation of prostatic epithelial cells induced by partially purified bone stromal conditioned media.

The above results indicated that bFGF was not responsible for the activity of the bone derived conditioned media. Further studies were conducted to confirm this using antibodies directed to purified growth factors. It was determined that the NbE-1 soft agar colony-forming efficiency of the active fraction could not be neutralized by antibodies to bFGF, KGF or HGF antibodies (FIG. 10). Moreover, immunoblotting of the active fraction with antibodies against bFGF, KGF, TGFβ$_1$, HGF, and EGF also failed to reveal any immunoreactive bands. These results together suggest that the above factors are probably not the endogenous growth factors in the conditioned media, and therefore, that certain unique growth factor(s) are largely responsible for such stimulatory activity.

It should be noted here, however, that the above results do not exclude the possible involvement of factors that may belong to one of the bFGF, KGF, TGFβ, HGF, or EGF families. In a separate study, the inventors have also shown that bFGF, HGF, and nerve growth factor (NGF) have certain growth-promoting effects on prostate cancer cells.

Due to the presence of several high M$_r$ protein species in the active fraction, western blot analyses of this fraction with antibodies raised against several (ECM) proteins, laminin, fibronectin, tenascin, and entactin were performed. The results demonstrated that this fraction reacted positively with fibronectin and tenascin, but not laminin and entactin antibodies. It is possible that the ECM proteins may act in concert with active growth factor(s), both of which may be necessary for inducing prostate cancer growth or progression.

In extending these analyses to two fresh bone marrow aspirate samples obtained from patients with prostate cancer (with confirmed bony metastasis) and lung cancer (without metastasis), it was found that fresh bone marrow aspirates from both patients contained similar tenascin antibody-reactive proteins to the conditioned media. However, a 110 kD (p110) protein was found to be present in the bone marrow aspirate of the prostate but not the lung cancer patient. This p110 could represent a tenascin proteolytic fragment. In addition to tenascin, fibronectin antibody also reacted selectively with some common proteins (banded at >228 kDa) present in both bone marrow samples and the conditioned media. The control media was found to be devoid of immunoreactivity with tenascin and fibronectin antibodies.

EXAMPLE 3

Further Characterization of Bone-Harrow Derived Growth Factors

This example demonstrates an approach which the inventors propose may be employed in the future characterization of the growth factors. The preferred approach recommended by the inventors involves the initial preparation of antibodies against the growth factor polypeptides.

To further characterize the biochemical nature of these human bone-derived growth factors, monoclonal antibodies (mAbs) will first be raised against the constituent polypeptides. The inventors propose the partially-purified growth factor preparation as a starting material for this procedure for the following reasons. Firstly, the action of the conditioned media cannot be neutralized using a single commercially available antibody directed against any of the known growth factors. Secondly, the total number of bone stromal cell-associated proteins in the partially purified fractions is relatively small, and it will be possible to develop specific mAbs against all of these proteins. Most importantly, fresh bone marrow supernatant fractions contain proteins similar to those of the conditioned media.

It is proposed that such mAbs will have utility in a variety of different embodiments. They will be powerful tools for the further purification of the growth factors. From the data presented above, it seems likely that the interaction between the growth factors, the prostate cancer cells, and certain ECM proteins may be required for prostate cancer progression and acquired behaviors such as metastatic and androgen-independent properties. mAbs against such polypeptides are therefore potentially attractive diagnostic, prognostic, imaging, and therapeutic agents for the treatment of prostate cancer in man. In that mAbs may be obtained which bind specifically to the cancer cells, or to cancer-specific antigens in circulation, such mAbs would also be a powerful diagnostic agent.

The conditioned media of the MS culture will be fractionated to prepare the partially purified growth factors against which mAbs are to be generated. An aliquot of this material will be loaded onto a heparin sepharose affinity column previously equilibrated an appropriate buffer, such as Tris HCl, (pH 7.4). Proteins will be eluted from the column by a continuously increasing NaCl gradient, and the concentration, mitogenic activity, and soft agar colony-forming efficiency of all fractions eluted from the column will be determined. The biologically active fractions will be pooled and concentrated by a suitable method, such as, for example, dialysis and lyophilization, or desalting using dry sephadex gels or sephadex gel exclusion column chromatography followed by lyophilization.

It is proposed that Balb/c mice of approximately 3 months in age will be immunized intraperitoneally (day 0) with 10 to 50 µg/mouse of the partially purified growth factors homogenized with Ribi mouse adjuvant system (Ribi, 1985). The mice will then be given two consecutive weekly intraperitoneal injections of the antigens mixed with Ribi mouse adjuvant (day 7 and 14). Approximately one month after the third injection, booster inoculation of antigens alone will be given. Here the inventors contemplate that the novel booster method described below will be advantageously employed. It is proposed that the immunized mice will be surgically opened to expose the spleen and a sterile solution of 5 to 20 µg of the growth factor antigens will be injected directly into the spleen. The mouse will then be sutured and allowed to recover. It is believed that this method will allow the optimal exposure of the splenocytes to the booster antigen.

Five to 7 days after the booster injection, a small amount of blood from the tail of the immunized mice will be bled and tested for the presence of circulating antibodies to the growth factors by an enzyme-linked immunosorbent assay (ELISA). Those mice producing reasonable titers of circulating antibodies to the partially purified antigens will be sacrificed and their spleens will be aseptically removed for cell fusion.

The mouse myeloma cell line proposed to be of use for hybridization is the 8-azaguanine-resistant mouse murine myeloma SP2/0 non-producer cell line. The SP2/0 cell line has been selected for S-azaguanine resistance and does not survive in medium containing hypoxanthine, aminopterin, and thymidine (HAT). The cells will be fused as described in (Chan et al., 1987). Immune splenocytes ($10^8$ cells) obtained from two hyperimmunized mice and 8-azaguanine-resistant SP2/0 mouse myeloma cells ($10^7$ cells) will be fused using 37% (v/v) polyethylene glycol 1500 (M.W. 500–600 M. A. Bioproducts, Inc.). Fused cells will be maintained for two days in growth medium that has been conditioned by SP2/0 cells, and then plated in five or six 96-well microtiter plates in growth medium containing HAT (selection medium) and screened for antibody production at the end of 2 weeks by indirect ELISA.

For the screening, purified growth factors, or partially purified growth-promoting factor(s) obtained from the conditioned media, or bone marrow supernatant fractions may be used as target antigens, and media plus NaCl may be used as a control. The target antigens (50 ng/50 µl/well) will be immobilized onto the bottoms of the 96-well microtiter plates by slow evaporation at 4° C. overnight. The culture medium from the wells propagating the splenocyte-myeloma (hybridoma) cells growing in the selection medium will be assayed for secreted antibodies that react with the immobilized antigens (either bone marrow supernatant fractions, or bone stromal cell-conditioned media, or purified growth factors may be used). The isotypes of the immunoglobulin(s) produced by cloned hybridoma cell clones may also be determined by ELISA, employing a commercial isotyping kit. The specificity of the mAbs may be determined by their reactivity with various antigens, as examined by ELISA and confirmed by western blot analysis.

After the mAbs are characterized, they may be produced in the form of mouse ascites fluid, purified and used to antagonize the soft agar colony forming efficiency of NbE-1 cells which are stimulated by the partially purified growth factors. This assay is proposed to be a reproducible, convenient and rapid assay method. Soft agar colony-forming efficiency is known to correlate directly with LNCaP tumorigenicity in vivo.

A mAb, termed MS 329, has been produced which has reactivity with a 157 kD growth factor polypeptide (FIG. 11).

Based on previous experience (Chi et al., 1987; Drewinko et al., 1986; Zhang et al., 1989), the inventors further propose that it will be possible to identify specific mAbs that may have diagnostic and prognostic values in predicting human prostate cancer metastasis to the bone, imaging the prostatic metastasis, and inhibiting tumor-stromal interaction. The criteria to be used in assaying for such mAbs are proposed to include tests for, e.g., specific reaction with a defined protein band of conditioned media in immunoblots or in immunohistochemical assays; and/or competition for the binding of the putative growth promoting factor(s) with the cell membrane fraction prepared from prostate cancer cell lines.

Once specific mAb(s) that meet the above criteria have been identified, the inventors contemplate their use in diagnosis, prognosis, imaging, and therapy. This approach is advantageous because, unlike any anti-PSA antibodies, the mAbs against cancer-specific antigens may not be trapped in the blood compartment and they would therefore more efficiently block prostate cancer and bone cellular interactions.

In addition, the inventors propose that the levels of these growth factors may correlate positively with prostate cancer progression. To investigate this, it is proposed that bone marrow aspirates will be obtained initially from late stages of the untreated prostate cancer patients (Stage D1, D2) and prostate cancer patients treated with hormonal therapy, or failed hormonal therapy, and chemotherapy. The concentration of growth factors in such samples may be analyzed by ELISA, or radioimmunoassay (RIA) and compared to the number of prostate cancer cells present in bone marrow.

The inventors propose that the concentrations of growth factors will correlate with the proliferative potential and aggressiveness of the prostate tumor in vivo and inversely with patients' survival, and may also predict the length of period of remission and disease-free survival. The concentration of these growth factors may also serve as a valuable index to predict cancer progression prior to the manifestation of clinical symptoms. It is believed that the ELISA or RIA assay contemplated by the inventors will be extremely sensitive. Based on immunoblot analysis of the growth factors, the sensitivity of this assay is estimated to be in the ng range. This sensitivity of assay could be used effectively to diagnose prostate cancer, or to predict the progression of prostate cancer and its response to various therapies in very small volumes of bone marrow aspirates. Similarly, the assay will be refined as a diagnostic tool for the early detection of the onset of prostate cancer.

In further embodiments, it is proposed that the mAb(s) will have utility in radio-imaging protocols. mAb(s) labeled with indium 111 (100) can be administered to mice previously inoculated with LNCaP and bone fibroblasts for the development of LNCaP tumors. In this manner the tumor can be imaged, the sensitivity determined, and the distribution of mAb-In 111 complex in this experimental model of prostate cancer examined. mAb(s) previously labeled with [$^{131}$I] or mAb-immunotoxins such as mAb-ricin A chain (Pearson et al., 1990) could be delivered through continuous infusion to mice which bear experimental LNCaP tumors and the outcome monitored.

The specific mAbs could also be employed in the rapid purification of the growth factor polypeptides following the creation of a mAb-affinity column. This could be achieved by conjugating a specific mAb to cyanogen bromide (CNBr) -activated sepharose CL4B (Pharmacia) (Chan et al., 1986; Li et al., 1987). As such, the antibodies would first be attached to the CNBr-sepharose, and the antisera-bound matrix then poured into a column and washed with a suitable wash buffer. An aqueous mixture including the growth factor polypeptides could then passed over the column under conditions to allow for immunocomplex formation between components in the mixture and the sepharose-bound antibodies. The column would then be washed extensively to remove non-specifically bound material and the specifically-bound antigens eluted from the column in a substantially purified state.

Such an affinity column could also be used to isolate and characterize growth-promoting component(s) from human bone marrow aspirates obtained from prostate cancer patients. In such embodiments, bone marrow aspirates (~10 ml per patient, at 20 to 30 mg protein/ml) could be obtained from prostate cancer patients, from female breast cancer patients (with or without bony metastasis), and from healthy normal male and female donors and analyzed. From such investigations, the sex-dependent differences and disease specificity of the growth factors that appear to promote human prostate tumor growth could be investigated.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Batson, O. V. The function of the vertebral veins and their role in the spread of metastasis. Ann. Surg. 112:138–149, 1940.

Berrettoni, B. A., and J. R. Carter. Mechanisms of cancer metastases to bone. J. Bone J. Surg. Am. 68A:308–312, 1986.

Camps, J. L., S. M. Chang, T. C. Hsu, M. R. Freeman, S. J. Hong, H. E. Zhau, A. C. von Eschenbach, and L. W. K. Chung. Fibroblast-mediated acceleration of human epithelial tumor growth in vivo. Proc. Natl. Acad. Sci. 87:75–79, 1990.

Canalis, E., T. McCarthy, and M. Centrella. Isolation and characterization of insulin-like growth factor I (somatomedin-C) from cultures of fetal rat calvariae. Endocrinology 122:22–27, 1988.

Capaldi et al., Biochem. Biophys. Res. Comm., 76:425, 1977.

Carter, H. B., and D. S. Coffey. The prostate: An increasing medical problem. The Prostate 16:39–48, 1990.

Chackel-Roy, M., C. Niemeyer, M. Moore, and B. R. Zetter. Stimulation of human prostatic carcinoma cell growth by factors present in human bone marrow. J. Clin. Invest. 84:43–50, 1989.

Chan, J. C., Keck, M. E., and Li, W. J. Biochem. Biophys. Res. Comm. 134:1223–1230, 1986.

Chang, S. M., and Chung, L. W. K. Interaction between prostatic fibroblast and epithelial cells in culture: Role of androgen. Endocrinology 125:2719–2727, 1989.

Chi, K. C., Scanlon, M. D., Henkel, R., Dreesman, G., Seo, J. S., Bowen, J. M. and Chan, J. C. Detection of human plasma-associated hepatitis (MAb): The same MAb can be used as both capture and tracer antibody. Diagnosis & Clin. Immunol. 5:91–99, 1987.

Chomcjymski, P., and N. Sacchi. Single step method of RNA isolation by acid guanidinium thiocyanate-phenol-chloroform extraction. Anal. Biochem. 162:156–159, 1987.

Chung, L. W. K., J. Matsura, and M. N. Runner. Tissue interaction and prostatic growth. I. Induction of adult mouse prostatic hyperplasia by renal urogenital sinus implants. Biol. Reprod. 31:155–163, 1984.

Chung, L. W. K., S. M. Chang, C. Bell, H. E. Zhau, J. Y. Ro, and A. C. von Eschenbach. Coinoculation of tumorigenic rat prostate mesenchymal cells with nontumorigenic epithelial cells results in the development of carcinosarcoma in syngeneic and athymic animals. Int. J. Cancer 43:1179–1187, 1989.

Cook, G. B., and F. R. Watson. Events in the natural history of prostate cancer: Using salvage curve, mean age distributions, and contingency coefficiences. J. Urol. 99:87–91, 1968.

Cunha, G. R., and L. W. K. Chung. Stromal-epithelial interactions: I. Induction of prostatic phenotype in urothelium of testicular feminized (Tfm/y) mice. J. Steroid Biochem. 14:1317–1321, 1981.

Davis, L. G., M. D. Dibner, and J. E. Battery. Rapid DNA preparation. In: Basic Methods in Molecular Biology. Elsevier Science Publishers, New York, 42–43, 1986.

DeCosse, J., C. L. Gossens, and J. F. Kuzma. Breast cancer: Induction of differentiation by embryonic tissue. Science 181:1057–1058, 1973.

Dedhar, S. Integrins and tumor invasion. Bioessays. 12:583–590, 1990.

Dickson, R. B., M. E. McManaway, and M. E. Lippman. Estrogen-induced factors of breast cancer cells partially replace estrogen to promote tumor growth. Science. 232:1540–1543, 1986.

Drewinko, B., Yang, L. Y., Chan, J. C., and Trujillo, J. M. New monoclonal antibodies against colon-cancer-associated antigens. Cancer Res. 46:5137–5143, 1986.

Elkin, M., and H. P. Mueller. Metastases from cancer of the prostate: Autopsy and roentgenological findings. Cancer 7:1246–1248, 1979.

Ensoli, B., S. Nakamura, S. Z. Salahuddin, P. Biberfeld, L. Larsson, B. Beaver, F. Wang-Staal, and R. C. Gallo. AIDS-Kaposi's sarcoma-derived cells express cytokines with autocrine and paracrine growth effects. Science 243:223–226, 1989.

Fidler, I. J., and G. L. Nicolson. Organ selectivity for implantation, survival and growth of B16 melanoma variant tumor lines. J. Natl. Cancer Inst. 57:1199–1202, 1976.

Ford, T. F., D. N. Butcher, J. R. W. Masters, and M. C. Parkinson. Immunocytochemical localization of prostate-specific antigen: Specificity and application to clinical practice. Br. J. Urol. 57:50–55, 1985.

Frank, L. M., P. N. Riddle, A. W. Carbonell, and G. O. Gey. A comparative study of the ultrastructure and lack of growth capacity of adult human prostate epithelium mechanically separated from its stroma. J. Pathol. 100:113–119, 1970.

Franks, L. M. The spread of prostatic carcinoma. J. Pathol. 73:603–611, 1956.

Gillies, R. J., N. Didier, and M. Denton. 1986. Determination of cell number in monolayer cultures. Anal. Biochem. 159:109–113, 1987.

Globus, R., J. Plouet, and D. Gospodarowicz. Cultured bovine bone cells synthesize basic fibroblast growth factor and store it in their extracellular matrix. Endocrinology 124:1539–1547, 1989.

Guthrie, P. D., Freeman, M. R., Liao, S., and Chung, L. W. K. Regulation of gene expression in rat prostate by androgen and β-adrenergic receptor pathways. Mol. Endocrinol. 4:1343–1353, 1990.

Hart, I. R. "Seed and soil" revisited: Mechanisms of site-specific metastasis. Cancer Metastasis Rev. 1:5–16, 1985.

Hauschka, P. V., A. E. Mavrakos, M. D. Iafrati, S. E. Soleman, and M. Klagsbrun. Growth factors in bone matrix: Isolation of multiple types by affinity chromatography on heparin Sepharose. J. Biol. Chem. 261:12665–12674, 1986.

Hodges, G. M., R. M. Hicks, and G. D. Spacey. Epithelial-stromal interactions in normal and chemical carcinogen-treated adult bladder. Cancer Res. 37:3720–3730, 1977.

Horak, E., D. Z. Darling, and D. Tarin. Organ specific effects on metastatic tumour growth studied in vitro. In: Treatment of Metastasis: Problems and Prospects. K. Hellman and S. A. Eccles, editors. Taylor and Francis, London. 369–372, 1985.

Horoszewicz, J. S., S. S. Leong, E. Kawinski, J. P. Kerr, H. Rosenthal, T. M. Chu, E. A. Mirand, and G. P. Murphy. LNCaP model of human prostatic carcinoma. Cancer Res. 43:1809–1818, 1983.

Hujanen, E. S., and V. P. Terranova. Migration of tumor cells to organ-derived chemoattractants. Cancer Res. 45:3517–3521, 1985.

Isaacs, J. T. Development and characteristics of available animal model systems for the study of prostate cancer. In: Current Concepts and Approaches to the Study of Prostate Cancer. D. S. Coffey, W. A. Gardner, Jr., N Bruchovsky, M. I. Resnick, and J. P. Karr, editors. Alan R. Liss, New York. 513–576, 1987.

Jacobs, S. C. Spread of prostatic carcinoma to bone. Urology 21:337–344, 1983.

Jacobs, S. C, D. Pikna, and R. K. Lawson. Prostatic osteoblastic factor. Invest. Urol. 17:195–198, 1979.

Janek, P., P. Briand, and N. R. Hartman. The effect of estrone-progesterone treatment on cell proliferation kinetics of hormone-dependent GR mouse mammary tumors. Cancer Res. 35:3698–3704, 1975.

Johnson, D. E. Cancer of the prostate: Overview. In: Genitourinary Tumors: Fundamental Principles and Surgical Techniques. D. E. Johnson, and M. A. Boileau, editors. Grune and Stratton, Inc., New York. 1–31, 1982.

Kabalin, J. N., D. M. Peehl, and T. A. Stamey. Clonal growth of human prostatic epithelial cells is stimulated by fibroblasts. The Prostate 14:251–263, 1989.

Kanamarus, H., and O. Yoshida. Assessment of in vitro lymphokine activated killer (LAK) cell activity against renal cancer cell lines and its suppression by serum factor using crystal violet assay. Urol. Res. 17:259–264, 1989.

Kratochwil, K. Tissue interactions during embryonic development. In: Tissue Interactions in Carcinogenesis. D. Tarin, editor. Academic Press, London. 1–47, 1972.

LaRocca, R. V., Stein, C. A. and Myers, C. E. Cancer Cells 2:106–115, 1990.

Li, W. J., Chi, K., Gallick, G., and Chan, J. C. Virology 156:91, 1987.

Lu, J., Y. Nishizawa, A. Tamaka, N. Nonomura, H. Yamanishi, N. Uchida, B. Sato, and K. Matsumoto. Inhibitory effect of antibody against basic fibroblast growth factor on androgen- or glucocorticoid-induced growth of Shionogi carcinoma 115 cells in serum-free culture. Cancer Res. 49:4963–4967, 1989.

Lundwall, A., and H. Lilja. Molecular cloning of human prostate specific antigen cDNA. FEBS Lett. 214:317–322. 1987

Manishen, W. J., K. Sivananthan, and F. W. Orr. Resorbing bone stimulates tumor cell growth: A role for the host microenvironment in bone metastasis. Am. J. Pathol. 123:39–45, 1985.

Miller, F. R., D. McEachern, and B. E. Miller. Growth regulation of mouse mammary tumor cells in collagen gel cultures by diffusible factors produced by normal mammary gland epithelium and stromal fibroblasts. Cancer Res. 49:6091–6097, 1989.

Mundy, G. R., S. DeMartino, and D. W. Rowe. 1981. Collagen and collagen-derived fragments are chemotactic for tumor cells. J. Clin. Invest. 68:1102–1105, 1982.

Mydlo, J. H., J. Michaeli, W. D. W. Heston, and W. R. Fair. Expression of basic fibroblast growth factors mRNA in benign prostatic hyperplasia and prostatic carcinoma. The Prostate. 13:241–247, 1988.

Nicolson, G. L., and J. L. Winkelhake. Organ specificity of blood-born tumour metastasis determined by cell adhesion. Nature 255:230–232, 1975.

Nicolson, G. Cancer metastasis. Sci. Am. 240:66–76, 1979.

Nishi, N., Y. Matuo, K. Kunitomi, I. Takenaka, M. Usami, T. Kotake, and F. Wada. Comparative analysis of growth factors in normal and pathologic human prostates. The Prostate 13:39–48, 1988.

Nonomura, N., N. Nakamura, N. Uchida, S. Noguchi, B. Sato, T. Sonoda, and K. Matsumoto. Growth-stimulating effect of androgen-induced autocrine growth factor(s) secreted from Shionogi carcinoma 115 cells on androgen-unresponsive cancer cells in a paracrine mechanism. Cancer Res. 48:4904–4908, 1988.

Paget, S. The distribution of secondary growths in cancer of the breast. Lancet 1:571–573, 1989.

Papsidero, L. D., M. Kuriyama, M. L. Wang, J. S. Horoszewicz, S. S. Leong, L. Valenzuela, G. P. Murphy, and T. M. Chu. Prostate antigen: A marker for human prostate epithelial cells. J. Natl. Cancer Inst. 66:37–42, 1981.

Pearson, J. W. Hedrick, E., Fogler, W. E., Bull, R. L., Ferris, D. K., Riggs, C. W., Wiltrout, R. H., Sivan, G., Morgan, A. C., Groves, E. and Longo, D. L. Cancer Res. 50:6379–6388, 1990.

Perkel, V. S., Mohan, S., Herring, S. J., Baylik, D. J., and Linkhart, T. A. Human prostate cancer cells, PC3, elaborate mitogenic activity which selectively stimulates human bone cells. Cancer Res. 50:6902–6907, 1990.

Picard, O., Y. Rolland, and M. F. Poupin. Fibroblast-dependent tumorigenicity of cells in nude mice: Implication for implantation of metastases. Cancer Res. 46:3290–3294, 1986.

Pitot, H. C., L. E. Grosso, and T. Goldsworthy. Genetics and epigenetics of neoplasia: Facts and theories. In: Carcinogenesis. E. Huberman and S. H. Barr, editors. Raven Press, New York, 65–69, 1985.

Potter, K. M., S. J. Juacaba, J. E. Price, and D. Tarin. Observations on organ distribution of fluorescein-labelled tumour cells released intravascularly. Invasion Metastasis 3:221–233, 1983.

Ribi E., Clinical Immunology Newsletter 6:33, 1985.

Sampath, T. K., M. Muthukumaran, and A. H. Reddi. 1987. Isolation of osteogenin, and extracellular matrix-associated bone-inductive protein, by heparin affinity chromatography. Proc. Natl. Acad. Sci. U.S.A. 84:7109–7113, 1986.

Schuurmans, A. L. G., J. Bolt, and E. Mulder. Androgen receptor-mediated growth and epidermal growth factor receptor induction in human prostate cell line LNCaP. Urol. Int. 44:71–76, 1989.

Shearman, P. J., W. M. Gallatin, and B. M. Longenecker. Detection of a cell-surface antigen correlated with organ-specific metastasis. Nature 286:267–269, 1980.

Shevrin, D. H., S. L. Kukreja, L. Ghosh, and T. E. Lad. Development of skeletal metastasis by human prostate cancer in athymic nude mice. Clin. Expl. Metastasis 6:401–409, 1988.

Sonnenschein, C., N. Olea, M. E. Pasanen, and A. M. Soto. Negative controls of cell proliferation: Human prostate cancer cells and androgens. Cancer Res. 49:3474–3481, 1989.

Stamey, T. A., N. Yang, A. R. Hay, J. E. McNeal, F. S. Frieha, and E. Redwine. Prostate-specific antigen as a serum marker for adenocarcinoma of the prostate. New. Engl. J. Med. 317:909–916, 1987.

Story, M. T., J. Sasse, S. C. Jacobs, and R. K. Lawson. Prostatic growth factor: Purification and structural relationship to basic fibroblast growth factor. Biochemistry. 26:3843–3849, 1987.

Thompson, J. A., K. D. Anderson, J. M. DiPietro, J. A. Zwiebel, M. Zarnetta, W.FK. Anderson, and T. Maciag. Site-directed neovessel formation in vivo. Science 241:1349–1352, 1988.

Varani, J. Chemotaxis of metastatic tumor cells. Cancer Metastasis Rev. 1:17–28, 1982.

Wergedal, J. E., S. Mohan, A. K. Taylor, and D. J. Baylink. Skeletal growth factor is produced by human osteoblast-like cells in culture. Biochem. Biophys. Acta. 889:163–170, 1986.

Wilding, G., E. Valverius, C. Knabbe, and E. P. Gelmann. Role of transforming growth factor-alpha in human prostate cancer cell growth. The Prostate 15:1–12, 1989.

Zhang, H. Z., Ordonez, N. G., Batsakis, J. G., and Chan, J. C. Monoclonal antibody recognizing a carcinoembryonic antigen epitope differentially expressed in human colonic carcinoma versus normal adult colon tissues. Cancer Res. 49:5766–5773, 1989.

What is claimed is:

1. A composition that promotes the growth of prostate cells in the presence of antibody against β-fibroblast growth factor, kerotinocyte growth factor, and hepatocyte growth factor, said composition consisting of eight proteins having molecular weights of about 227, 223, 218, 157, 90, 80, 48, and 20 kD, respectively, as assessed under non-reducing conditions on SDS-PAGE, the composition obtained by:

a) culturing human bone stromal cells in serum-free medium to produce conditioned mediim;

b) passing said conditioned medium over a heparin affinity column in a low salt-containing buffer 10 mM Tris/HCl;

c) washing the column;

d) eluting the eight proteins from the column with a buffer containing 1M NaCl.

* * * * *

UNITED STATES PATENT AND TRADEMARK OFFICE
CERTIFICATE OF CORRECTION

PATENT NO.    :    5,679,636

DATED         :    October 21, 1997

INVENTOR(S)   :    Leland W.K. CHUNG et al.

It is certified that error appears in the above-identified patent and that said Letters Patent is hereby corrected as shown below:

Column 5, line 24, please replace "nontumorigenic" with --non-tumorigenic--; and
    lines 52-53, please replace "nontu-morigenic" with --non-tumorigenic--.
Column 7, line 16, please replace "S-azaguanine" with --8-azaguanine--.
Column 14, line 36, please replace "Androgon" with --Androgen--.
Column 15, line 34, please replace "sarconatous" with --sarcomatous--.
Column 17, line 26, please replace "vive" with --vivo--.

Signed and Sealed this

Twenty-eighth Day of April, 1998

*Attest:*

BRUCE LEHMAN

*Attesting Officer*       *Commissioner of Patents and Trademarks*